US009814822B2

(12) United States Patent
Doyle et al.

(10) Patent No.: US 9,814,822 B2
(45) Date of Patent: Nov. 14, 2017

(54) PLASMA GENERATION WITH DIALYSIS SYSTEMS

(71) Applicant: Fresenius Medical Care Holdings, Inc., Waltham, MA (US)

(72) Inventors: Matthew Doyle, Concord, CA (US); Alexander Joseph Brown, Danville, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 73 days.

(21) Appl. No.: 14/837,769

(22) Filed: Aug. 27, 2015

(65) Prior Publication Data
US 2017/0056576 A1    Mar. 2, 2017

(51) Int. Cl.
| | | |
|---|---|---|
| A61M 1/34 | (2006.01) | |
| A61M 1/36 | (2006.01) | |
| B01D 61/24 | (2006.01) | |
| A61M 1/16 | (2006.01) | |

(52) U.S. Cl.
CPC ........ *A61M 1/3496* (2013.01); *A61M 1/1633* (2014.02); *A61M 1/3413* (2013.01); *A61M 1/3479* (2014.02); *A61M 1/3679* (2013.01); *A61M 2205/3334* (2013.01)

(58) Field of Classification Search
None
See application file for complete search history.

(56) References Cited

U.S. PATENT DOCUMENTS

| | | | | |
|---|---|---|---|---|
| 4,350,594 A | * | 9/1982 | Kawai | A61M 1/3472 210/110 |
| 4,980,297 A | | 12/1990 | Haynes et al. | |
| 5,744,042 A | * | 4/1998 | Stange | A61M 1/1654 210/644 |
| 6,439,845 B1 | | 8/2002 | Veres | |
| 6,858,146 B1 | | 2/2005 | Myers et al. | |
| 7,066,900 B2 | | 6/2006 | Botto et al. | |
| 7,169,303 B2 | | 1/2007 | Sullivan et al. | |
| 8,496,606 B2 | | 7/2013 | Leonard et al. | |
| 2011/0094962 A1 | | 4/2011 | Heinrich et al. | |
| 2012/0283628 A1 | | 11/2012 | Houwen et al. | |
| 2013/0062283 A1 | | 3/2013 | Peters et al. | |
| 2013/0131423 A1 | | 5/2013 | Wang et al. | |

FOREIGN PATENT DOCUMENTS

| | | | | | |
|---|---|---|---|---|---|
| DE | WO 0158496 A1 | * | 8/2001 | ......... | A61M 1/3472 |
| WO | WO 2011/133287 A1 | | 10/2011 | | |

OTHER PUBLICATIONS

Fresenius Medical Care, "plasmaFlux PSu," Therapeutic Apheresis, 2004, 4 pp.

* cited by examiner

*Primary Examiner* — Krishnan S Menon
(74) *Attorney, Agent, or Firm* — Fish & Richardson P.C.

(57) ABSTRACT

Embodiments for a blood plasma and red blood cell generation device are disclosed. The device may operate as an alternative modality of the dialysis machine, as part of the dialysis machine and/or as an add-on module. The fluid handling components of the plasma generation system may be integrated with a microprocessor unit for controlling and executing generation of plasma, or a control unit of the dialysis machine may be adapted to control the plasma generation aspects of the treatment.

19 Claims, 8 Drawing Sheets

PLASMA GENERATION WITH DIALYSIS SYSTEMS

TECHNICAL FIELD

This application generally relates to a biological fluid processing system and methods thereof, and, more specifically, to a system, method and apparatus for generation of blood plasma and red blood cells from whole blood.

BACKGROUND OF THE INVENTION

Blood processing systems and methods used to generate plasma typically withdraw whole blood from a patient. The whole blood is then directed to a separator, such as a centrifugal or membrane assembly, for separation of the plasma from the remaining blood components. In most cases, after collecting the plasma the remaining separated constituent components are returned to the patient together with one or more fluids to replace the plasma retained by the system. In the plasma collection procedure, it is generally desired to maintain a patient's fluid balance such that the difference between the amounts of removed fluid and replaced fluid is within a desired range.

There two common separators used in the process of plasma separation—a centrifuge or a plasma filter. When plasma is generated through use of a centrifuge, there are two plasmapheresis methods available: discontinuous flow centrifugation and continuous flow centrifugation. In discontinuous flow centrifugation, a discrete amount of blood is removed (approximately 300 ml) from the patient. Once the blood has been removed, blood plasma is separated through the action of the centrifuge, the non-plasma components are returned to the patient, and the plasma is collected. An advantage of discontinuous flow centrifugation is that only one venous line is required as blood is not removed until the centrifuge has generated the plasma and returned the non-plasma components to the patient. In continuous flow centrifugation, two venous lines are used to allow for concurrent removal of blood and return of non-plasma constituents to the patient. An advantage to this is that it can occur continuously.

The other common plasma separator is a plasma filter. When a plasma filter is used to generate plasma, this plasmapheresis method is generally referred to as plasma filtration. During plasma filtration, two venous lines are used to collect plasma through standard hemodialysis methods.

Hemodialysis is a process which employs a machine that includes a dialyzer with a semipermeable membrane to aide renal patients in the process of urea removal. The membrane serves to divide the dialyzer into two chambers. Blood is pumped through one chamber and a dialysis solution through the second. As the blood flows by the dialysis fluid, impurities, such as urea and creatinine, diffuse through the semipermeable membrane into the dialysis solution. Other purification techniques and processes may additionally be used. One such example is hemodiafiltration, which combines standard dialysis and hemofiltration into one process, whereby convective and diffusive clearance are achieved through the use of substitution fluid.

In the case of plasma filtration, a specialized dialyzer, i.e. a plasma dialyzer, is used instead of a standard dialyzer. The difference between these two types of dialyzers is the pore size of the dialyzer fibers. Typically, a standard dialyzer has fibers with a pore size cut off around 60,000 daltons to minimize the loss of desired blood components such as albumin, whereas a plasma dialyzer has fibers with a pore size greater than 60,000 daltons.

In standard dialysis, fresh dialysate solution, generally composed of reverse osmosis water, salt concentrate, and bicarbonate concentrates enters into one of the two dialysate ports of the dialyzer. The removal of uremic toxins is accomplished by diffusion resultant of the establishment of a concentration gradient between the blood in the inner chamber of the dialyzer and the dialysate in the outside chamber of the dialyzer. After diffusion of uremic toxins from the blood across the semipermeable into the dialysate occurs, the spent dialysate solution exits the second dialysate port of the dialyzer and is returned to the machine to be discarded. Additionally, in some cases the spent dialysate is directed to a re-use cartridge, such as a sorbent cartridge, so that the spent dialysate can be re-incorporated into the fresh dialysate stream after purging the associated uremic toxins.

In plasma filtration, blood enters into a plasma dialyzer with dialyzer fibers with pore size that exceeds that of a standard dialyzer. As a result, albumin, along with the plasma itself is easily capable of traversing the semipermeable membrane of the dialyzer and only larger molecular weight molecules such as red blood cells are prevented from traversing the membrane. Examples of such filters include the Evacure and Evaclio plasma separators from LINC medical, the Monet filter from Fresenius Medical Care, and the PlasmaFlo™ from Apheresis Technologies, Inc.

As a result of the distinction in the use of the dialyzer, the two dialysate ports are not used in an analogous way to dialysis. Instead of fresh dialysate entering one port and spent dialysate exiting the other, a portion of the blood plasma travels across the semipermeable membrane and exits one port of the dialyzer. The second dialyzer port is either not used, or used as a port to monitor pressure. Substitution fluid or saline must be introduced immediately after the plasma dialyzer through use of a fluid pump to replace the plasma that traverses the semipermeable membrane to maintain fluid balance. Additionally, the substitution fluid aides in the flow of the red-blood cells through the plasma dialyzer by reducing the hematocrit in the red-blood cell/plasma solution that exits the blood outlet port of the dialyzer. The intent of this substitution fluid addition is to maintain the hematocrit of the red-blood cell/plasma solution exiting the dialyzer.

It also is generally the case for plasma filtration that a plasma pump is located downstream of the dialyzer port where the plasma exits the dialyzer. The purpose of this pump is to help facilitate the movement of the blood plasma through use of the pump with concurrent monitoring of the pressure in the plasma dialyzer at the second dialysate port. An anticoagulant such as Citrate or Heparin is also generally used for standard dialysis, plasma filtration, and continuous/discontinuous flow centrifugation. If it were desired to collect red blood cells instead of blood plasma, similar limitations may apply.

A limitation of plasma filtration is that the rate of plasma generated at the output of the plasma dialyzer dialysate port can only be a fraction of the input rate of whole blood into the dialyzer. This is because a fraction of the blood plasma will also exit through the blood outlet of the plasma dialyzer along with the red blood cell solution.

Accordingly, it would be desirable to provide a more efficient plasma generation method that may generate plasma at a rate approaching the rate of whole blood entering into the plasma dialyzer. It would also be desirable to provide a plasma generation method that does not require a plasma pump to facilitate the movement of blood plasma or a saline pump to maintain fluid balance, yet may still facilitate the movement of plasma across the semipermeable membrane in an analogous way.

Additionally, it would be desirable to provide a more efficient technique of red blood cell generation that does not require a plasma pump to facilitate the movement of blood plasma or a saline pump to maintain fluid balance.

Further, it would also be desirable to enhance current plasmadiafiltration techniques.

SUMMARY OF THE INVENTION

According to the system described herein, a continuous plasma and red blood cell generation method and device are provided that do not require the use of a plasma pump. The system described herein provides for a continuous plasma and red blood cell generation method capable of generating plasma at a rate approaching the rate that whole blood entering into the plasma dialyzer.

The system described herein may be embodied in a modified dialysis machine which is adapted to perform plasma filtration and plasmadiafiltration in accordance with the system described herein. The modified dialysis machine may be adapted through utilization of a plasma generation module bay along with the required hydraulic changes. In this way, existing hemodialysis machines, such as the Fresenius 2008T machine, may be upgraded in the field to execute the plasma generation method described herein. Alternatively, the system described herein may be embodied in a "stand-alone" device. Further, the system described herein may be embodied in an "add-on" system which may be used in conjunction with a standard UF controlled dialysis, machine to perform plasma filtration and plasmadiafiltration according to the system described herein.

A plasma generation device in accordance with an embodiment of the system described herein may include at least two dialyzers. The first dialyzer may be a plasma dialyzer, and the second dialyzer may be a standard dialyzer located downstream of the outlet dialysate port of the plasma dialyzer in the extracorporeal circuit. Additionally, a dialysis machine with the ability to generate dialysate and also equipped with a control unit to control fluid (dialysate, substitution fluid, and blood) flow rates may be included. The embodiment may also be set-up in an optional modality to collect red-blood cells instead of blood plasma.

In an embodiment of the system described herein, the two dialyzers may each contain a semipermeable membrane, and in the system described herein may be aligned in a series wherein blood plasma, produced by the first plasma dialyzer, is directed to the second dialyzer located downstream of the first plasma dialyzer. The control unit may contain various pumps, pressure monitoring devices, valves, electronic components, connector fittings, tubing, etc., as required in order to coordinate the operation of the other system components.

Blood enters the bloodside compartment of the first plasma dialyzer. Concurrently, unlike traditional methods of plasma filtration, a fresh dialysate line is connected to one of the two dialysate ports of the plasma dialyzer resulting in dialysate being introduced into the dialysate-side compartment. Resultant of the introduction of dialysate through the fresh dialysate port of the plasma dialyzer, the rate at which plasma traverses the semipermeable membrane will be increased by the diffusive clearance through use of dialysate due to the concentration gradient of the plasma constituents established through use of the dialysate.

Convective clearance in the system described herein may also occur through the introduction of dialysate through the plasma dialyzer in a way more analogous to hemodiafiltration, rather than through use of a plasma pump without dialysate in a method more analogous to hemofiltration as is the case for current plasma filtration methods. Because hemodiafiltration requires sterile substitution fluid, and due to the fact that the dialysate fluid introduced in the first plasma dialyzer may mix with the blood plasma in an analogous way to substitution fluid incorporated into whole blood, a second sterility filter dedicated to the fresh dialysate line connected to the plasma dialyzer may be desirable to supply substitution fluid (rather than dialysate) to the plasma dialyzer.

The fresh dialysate or substitution fluid supplied to the plasma dialyzer enters concurrently, and runs parallel to the blood flow direction. The majority of the blood plasma traverses the semipermeable membrane, and the plasma along with the dialysate (or substitution fluid) exits the dialysate port of the plasma dialyzer. Red blood cells, which are incapable of traversing the semipermeable membrane, exit the blood outlet of the dialyzer along with the fraction of the dialysate or substitution fluid and blood plasma not associated with the blood plasma exiting the second dialysate port.

Typically, plasma generations methods such as those implemented by the Monet Set-up System of Fresenius rely on two pumps downstream of the point of plasma generation. One pump is used to facilitate the movement of plasma across the semipermeable membrane in a method analogous to hemofiltration. The second pump is used to introduce saline or substitution fluid to minimize increases in Hematocrit at the outlet of the plasma dialyzer resultant of the removal of the plasma from the whole blood. A pump dedicated to the introduction of saline is not required in the system described herein, as the dialysate (or substitution fluid) introduced in the plasma dialyzer may instead mitigate the reduction of relative blood volume at the red blood cell outlet of the plasma dialyzer. Similarly, the dialysate (or substitution fluid) introduced in the plasma dialyzer may also remove the necessity of a pump to facilitate the movement of plasma—as plasma filtration may occur through convective clearance resultant of the introduction of substitution concurrently. Diffusion additionally facilitates the movement of plasma across the semipermeable membrane of the plasma dialyzer.

In an embodiment of the system described herein, restriction valves may be located downstream of the both the dialysate port outlet and the blood port outlet of the plasma dialyzer. The restriction valve located downstream of the output dialysate port of the plasma dialyzer may restrict the fluid flow to ensure that a desired flow rate is achieved at the blood outlet of the plasma dialyzer to ensure the red blood cell/dialysate/plasma fluid flows at a minimum and/or controlled rate. The restriction valve located downstream of the blood outlet may serve an analogous purpose by ensuring a minimum and/or controlled flow rate of the blood plasma constituents is achieved at the outlet of the second dialysate port of the plasma dialyzer.

Through use of the two restriction valves, the flow rate of the plasma/dialysate fluid is prevented from exceeding a desired threshold; moreover, the flow rate of the red blood cell/dialysate/plasma fluid is controlled to be within a desired threshold. It is desired that the flow rate of the plasma/dialysate exiting the dialysate port outlet of the plasma dialyzer approaches the flow rate of whole blood into the plasma dialyzer. This ensures that the plasma exiting the second dialysate port of the plasma dialyzer contains approximately the same concentration of plasma constituents not present in the dialysate (ex. proteins, hormones). It is also desired that the flow rate of the red blood cell/dialysate/plasma fluid exiting the blood port of the plasma dialyzer not exceed the flow rate of the whole blood entering into the plasma dialyzer yet also be maintained above a desired threshold to ensure maximized plasma generation. The restriction valve located downstream of the blood outlet of the plasma dialyzer minimizes the amount of plasma and dialysate capable of exiting the blood outlet—thus ensuring that the majority of plasma exits the outlet of the second dialysate port of the plasma dialyzer. In an embodiment of the system described herein, the restriction valve also ensures a desired flow rate at the outlet of a second dialyzer located downstream of the plasma dialyzer is achieved.

In an embodiment of the system described herein, blood plasma exiting the dialysate port outlet of the plasma dialyzer enters into the bloodside compartment of the second dialyzer. Fresh dialysate from a first fresh dialysate line may supply dialysate or substitution fluid to the plasma dialyzer and dialysate from a second fresh dialysate line enters concurrently into the dialysate-side compartment of the second standard dialyzer, and runs parallel or counter-parallel to the blood plasma flow direction. Through use of a balancing system (such as those seen in the 2008 or 4008 by the company Fresenius Medical Care, the machine Centry 3 of company Cobe, the machine System 1000 of company Althin Medical, the machine MIRO-CLAV of company Baxter, or the machine DIALOG of company B. Braun-Melsungen) and an ultrafiltration pump, constituents of the plasma capable of traversing the dialyzer pores of the semipermeable membrane of the second dialyzer enter into the dialysate-side compartment. The second fresh dialysate line may connect in parallel to the first dialysate line supplying dialysate or substitution fluid to the plasma dialyzer. Through use of two valves or a three-way valve, the exact flow rates of fresh dialysate delivered from the balancing chamber to the first and second dialysate lines can be controlled through software duty-cycling of the valves. Pressures may be monitored both on the bloodside and the dialysate side of each dialyzer cartridge as a way to determine transmembrane pressure (TMP) across each dialyzer.

In order to maintain the appropriate fluid balancing in the balancing system, it is necessary that sum of the amount of fresh dialysate or substitution fluid supplied at the first plasma dialyzer and the fresh dialysate supplied at the second dialyzer must be concurrently removed from the second dialyzer. The ultrafiltration pump can additionally be used in the conventional manner, if desired, to reduce relative blood volume of the patient.

In an embodiment, plasma exiting the second dialyzer may enter into a plasma bag for collection. The plasma bag may be equipped with an air-permeable filter, such as a Gore-tex filter, to allow for the venting of air, but not fluids in the plasma collection bag. Additionally, pressure sensing in the extracorporeal circuit allows for termination of the plasma generation process when a desired pressure is detected in the plasma collection bag.

In another embodiment, plasma exiting the outlet of the plasma dialyzer may enter a recirculation loop. Through the driving force of an additional blood plasma pump connecting the extracorporeal circuit directly after the second dialyzer to the extracorporeal circuit directly before the second dialyzer, the plasma in the recirculation loop may be repeatedly cycled through the second dialyzer. Through recirculation of blood plasma through the second dialyzer, undesirable components such as uremic toxins may be effectively eliminated. This allows for plasma suitable for donation to be generated from patients with higher levels of uremic toxins such as renal patients undergoing hemodialysis.

In yet another embodiment, an adsorbent cartridge (such as a Sorbent Cartridge of Fresenius Medical Care), may be present in the extracorporeal circuit downstream of the plasma dialyzer. The location of the adsorbent cartridge may be either before, or after the second dialyzer. An advantage of locating the adsorbent cartridge upstream of the second dialyzer is that it may reduce the concentrate of specific plasma constituents, such as urea in the case of a sorbent adsorbent cartridge, before entering the second dialyzer.

An advantage of locating the adsorbent cartridge downstream of the second dialyzer may be that the flow rate of the blood plasma in the extracorporeal circuit between the plasma dialyzer and second dialyzer may at no point be rate-limited by the output of the adsorbent cartridge. Since the fresh dialysate introduced in the first plasma dialyzer and second dialyzer must exit the spent dialysate port of the second dialyzer to maintain fluid balance, locating the adsorbent downstream of the second dialyzer eliminates the risk of the adsorbent cartridge potentially rate-limiting the spent dialysate flow rate in the second dialyzer—and as a result rate-limiting the ability to providing fresh dialysate to the plasma dialyzer. The rationale above is analogous for why locating the adsorbent cartridge before or after the recirculation loop in an embodiment of the system described herein may be desirable.

The spent dialysate from the second standard dialyzer is transported back to the dialysis machine. The UF Pump will generate convective clearance in the second dialyzer. Through use of valve duty-cycling on the fresh dialysate valves associated with each fresh dialysate line, the amount of fresh dialysate supplied to the first and second dialyzer can be controlled.

A plasma generation device in accordance with an alternative embodiment of the system described herein may include at least one dialyzer. The dialyzer may be a plasma dialyzer. Additionally, a machine with the ability to generate substitution fluid and also equipped with a control unit to control fluid (substitution fluid and blood) flow rates may be included. In this embodiment, substitution fluid generated from a machine without a balancing chamber may enter into the plasma dialyzer. Through use of the substitution fluid generation machine with a balancing chamber, a second dialyzer may not be required to maintain fluid balance in the dialysis machine. As a result, the second dialyzer may be eliminated; however, a recirculation loop may no longer be necessary or desirable and the blood plasma may enter into a plasma bag for collection. The embodiment may also be set-up in an optional modality to collect red-blood cells instead of blood plasma.

A plasma generation device in accordance with an alternative embodiment of the system described herein may include at least two dialyzers. The first dialyzer may be a plasma dialyzer, and the second dialyzer located downstream of the outlet blood port of the plasma dialyzer in the extracorporeal circuit may be a standard dialyzer. Additionally, a dialysis machine with the ability to generate dialysate and also equipped with a control unit to control fluid (dialysate, substitution fluid, and blood) flow rates may be included. Through placement of the second dialyzer at the blood outlet of the plasma dialyzer, the red blood cell/dialysate/plasma fluid travels through the second dialyzer instead of separated blood plasma. The rationale for such an embodiment is to allow for uremic toxins associated with the red blood cells to disassociate and be removed by the second dialyzer. This embodiment may also be set-up in an optional modality to collect red-blood cells instead of blood plasma.

In accordance with another embodiment of the system described herein, a hemodialysis/plasma generation machine may include at least three dialyzers. The first dialyzer may be a plasma dialyzer, the second dialyzer located downstream of the outlet dialysate port of the plasma dialyzer in the extracorporeal circuit may be a standard dialyzer, and the third dialyzer may be a standard dialyzer arranged in parallel with the above mentioned first and second dialyzers. The third dialyzer may allow for concurrent hemodialysis, while the first and second dialyzers allow for plasma filtration, and plasmadiafiltration. Additionally, a dialysis machine with the ability to generate dialysate and also equipped with a control unit to control fluid (dialysate, substitution fluid, and blood) flow rates may be included. The embodiment may also be set-up in an optional modality to collect red-blood cells instead of blood plasma.

BRIEF DESCRIPTION OF THE DRAWINGS

Embodiments, advantages, and features of the system described herein are explained with reference to the several figures of the drawings, which are briefly described as follows.

DETAILED DESCRIPTION OF VARIOUS EMBODIMENTS

Figure 1:
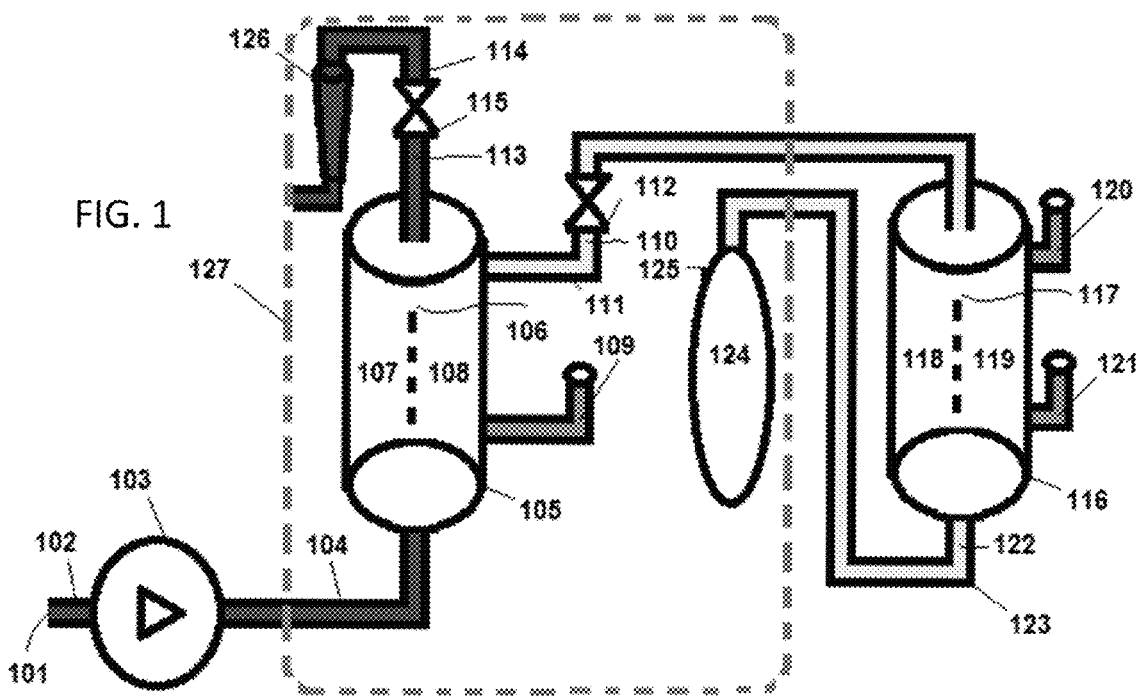
FIG. 1 is a schematic illustration of an extracorporeal blood circuit of a blood plasma and red blood cell generation device configured for generating blood plasma in accordance with a first embodiment of the system described herein.

The blood plasma and red blood cell generation method and device of the system described herein is principally described herein in the context of a stand-alone blood plasma and red blood cell generation machine. Additionally and/or alternatively, however, it is also explicitly noted that the system described herein may provide for a blood plasma and red blood cell generation module which can be incorporated into existing hemodialysis machines with minimal retrofitting to allow for the ability to execute plasma generation or red blood cell collection.

In accordance with a first embodiment of the system described herein, as described in more detail herein with reference to FIGS. 1, 3, 4, 5, 11, and 13, a blood plasma and red blood cell generation device includes a first and a second dialyzer. In this embodiment, the blood plasma and red blood cell generation device includes at least one sterility filter, which may contain semipermeable membranes for removing bacteria, endotoxins, and other particulate from the dialysate to generate suitable substitution fluid. The extracorporeal blood circuit contains various pumps, pressure monitoring devices, valves, electronic components, connector fittings, tubing, etc., as required. Preparation of dialysate solution includes mixing of water with dialysate concentrates. Water is generated using a suitable method of pre-treatment (ex. Reverse Osmosis). The dialysate fluid generated from the balancing chamber is partitioned, through use of valves and valve duty-cycling, for two sources: 1) The fresh dialysate of the first plasma dialyzer, and 2) The fresh dialysate of the second standard dialyzer. After being partitioned, fresh dialysate enters both the first and second dialyzer, concurrently, and runs parallel to the blood flow direction in the first specialized dialyzer and runs parallel or counter-parallel to the blood plasma (or red blood cells) generated by the first plasma dialyzer in the second dialyzer. The dialysate fluid in the first dialyzer provides diffusive and convective clearance and the dialysate fluid in the second dialyzer acts to provide a concentration gradient for the blood plasma (or red blood cells) in the second dialyzer thereby facilitating diffusion of uremic toxins across the semipermeable membrane. Spent dialysate exiting the second dialyzer is transported back to the plasma generation device.

Sterile/non-pyrogenic substitution fluid for use in a modality of an embodiment of the system described herein is prepared by drawing a portion of fresh dialysate solution from the dialysate inlet line and pumping it through a sterile filter cartridge. Through use of an additional sterile filter for the dialysate, the substitution fluid is effectively double filtered before introduction into the blood stream. The dialysis machine used to facilitate plasma generation in the system described herein may perform all of its normal functions, such as monitoring flow rates and pressures, controlling net ultrafiltration, monitoring used dialysate for blood presence, etc.

The blood plasma and red blood cell generation device of the system described herein operates as an alternative modality of the dialysis machine, as part of the dialysis machine or as an add-on module. The fluid handling components of the plasma generation system may be integrated with a microprocessor unit for controlling and executing generation of plasma, or a control unit of the dialysis machine may be adapted to control the plasma generation aspects of the treatment.

In accordance with a second embodiment of the system described herein, as described in more detail herein with reference to FIGS. 2, 6, 12, and 14, a blood plasma and red blood cell generation device includes a first and a second dialyzer. In this embodiment, the blood plasma and red blood cell generation device includes at least one sterility filter, which may contain semipermeable membranes for removing bacteria, endotoxins, and other particulate from the dialysate to generate suitable substitution fluid. The extracorporeal blood circuit contains various pumps, pressure monitoring devices, valves, electronic components, connector fittings, tubing, etc., as required. Preparation of dialysate solution includes mixing of water with dialysate concentrates. Water is generated using a suitable method of pre-treatment (ex. Reverse Osmosis). The dialysate fluid generated from the balancing chamber is partitioned, through use of valves and valve duty-cycling, for two sources: 1) The fresh dialysate of the first plasma dialyzer, and 2) The fresh dialysate of the second standard dialyzer. After being partitioned, fresh dialysate enters both the first and second dialyzer, concurrently, and runs parallel to the blood flow direction in the first specialized dialyzer and runs parallel or counter-parallel to the blood plasma (or red blood cells) generated by the first plasma dialyzer in the second dialyzer. The dialysate fluid in the first dialyzer provides diffusive and convective clearance and the dialysate fluid in the second dialyzer acts to provide a concentration gradient for the blood plasma (or red blood cells) in the second dialyzer thereby facilitating diffusion of uremic toxins across the semipermeable membrane. Spent dialysate exiting the second dialyzer is transported back to the plasma generation device.

In accordance with a third embodiment of the system described herein, as described in more detail herein with reference to FIGS. 7, 8, 15, and 16, a blood plasma and red blood cell generation device includes a first dialyzer. In this embodiment, the blood plasma and red blood cell generation device includes at least one sterility filter, which may contain semipermeable membranes for removing bacteria, endotoxins, and other particulate from the dialysate to generate suitable substitution fluid. The extracorporeal blood circuit contains various pumps, pressure monitoring devices, valves, electronic components, connector fittings, tubing, etc., as required. Preparation of dialysate solution includes mixing of water with dialysate concentrates. Water is generated using a suitable method of pre-treatment (ex. Reverse Osmosis). The dialysate fluid generated may run parallel to the blood flow direction. The dialysate fluid in the first dialyzer provides diffusive and convective clearance.

Figure 9:
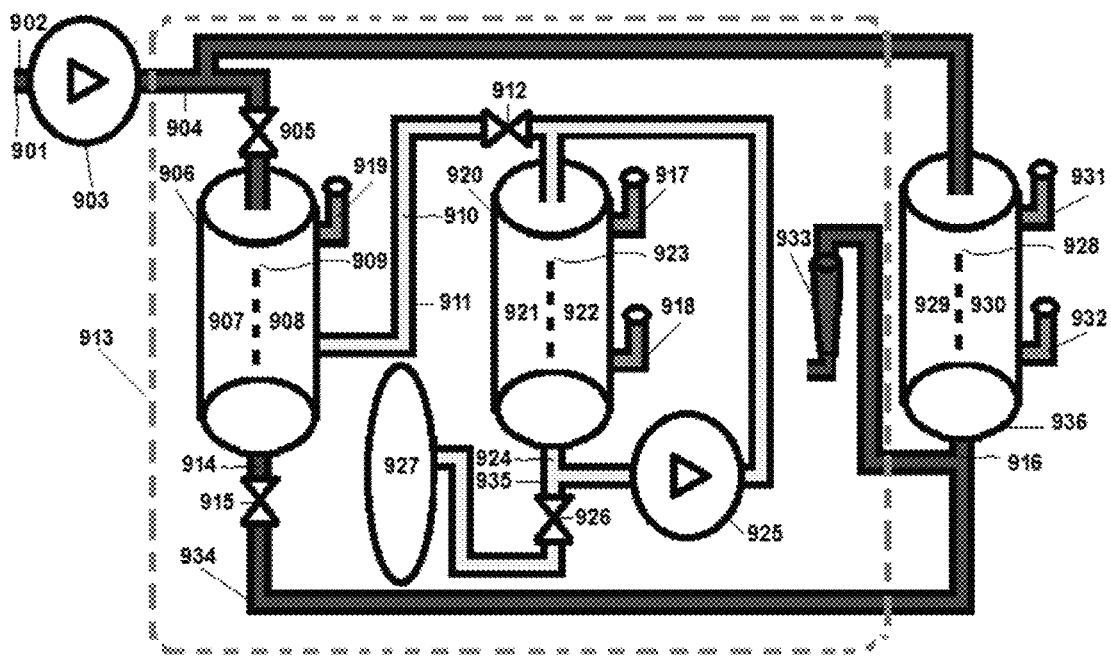
FIG. 9 is a schematic illustration of an extracorporeal blood circuit of a plasma generation and hemodialysis device system in accordance with a fourth embodiment of the system described herein.
Figure 10:
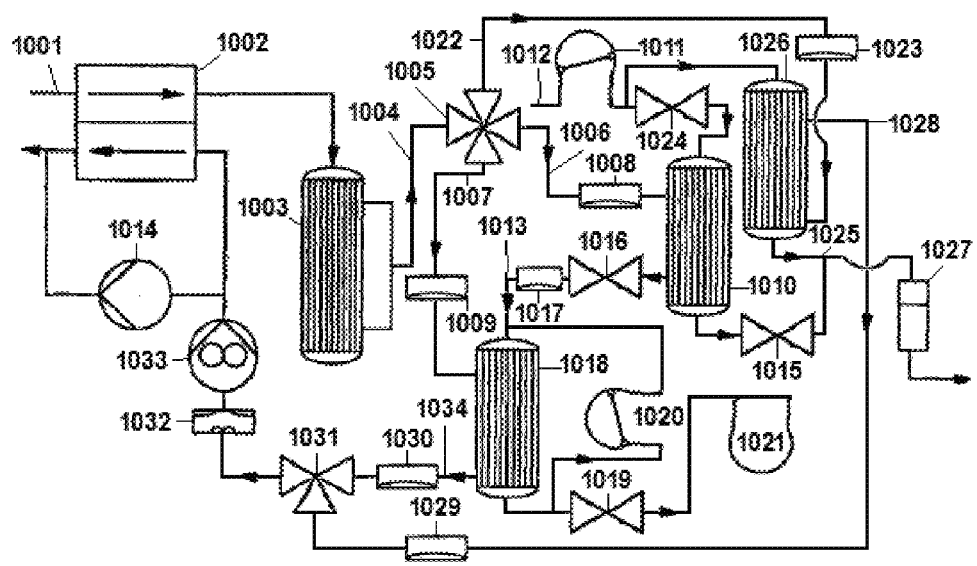
FIG. 10 is schematic illustration of a plasma generation and hemodialysis device system in accordance with the fourth embodiment of the system described herein.

In accordance with a fourth embodiment of the system described herein, as described in more detail herein with reference to FIGS. 9 and 10, a blood plasma and red blood cell generation device includes a first, a second, and a third dialyzer. In this embodiment, the blood plasma and red blood cell generation device includes at least one sterility filter, which may contain semipermeable membranes for removing bacteria, endotoxins, and other particulate from the dialysate to generate suitable substitution fluid. The extracorporeal blood circuit contains various pumps, pressure monitoring devices, valves, electronic components, connector fittings, tubing, etc., as required. Preparation of dialysate solution includes mixing of water with dialysate concentrates. Water is generated using a suitable method of pre-treatment (ex. Reverse Osmosis). The dialysate fluid generated from the balancing chamber is partitioned, through use of valves and valve duty-cycling, for three sources: 1) The fresh dialysate of the first plasma dialyzer, 2) the fresh dialysate of the second standard dialyzer, and 3) the fresh dialysate of the third standard dialyzer. After being partitioned, fresh dialysate enters the first, second, and third dialyzer, concurrently, and runs parallel to the blood flow direction in the first specialized dialyzer, runs parallel or counter-parallel to the plasma generated by the first plasma dialyzer in the second dialyzer, and runs parallel or counter-parallel to the whole blood in the third dialyzer. The dialysate fluid in the first dialyzer provides diffusive and convective clearance and the dialysate fluid in the second and third dialyzer acts to provide a concentration gradient for the blood plasma in the second dialyzer and the whole blood in the third dialyzer thereby facilitating diffusion of uremic toxins across the semipermeable membrane of the second and third dialyzer. Spent dialysate exiting the second and third dialyzer is transported back to the plasma generation device.

In the case of each of the first, second, third and fourth embodiments, the machine may provide an informational message and/or corresponding set-up instructions to ensure that the machine is correctly set-up for either a plasma collection or a red-blood cell collection mode.

Additionally, in the case where the embodiments are embodied in the form of a module bay machine add-on, the absence of the blood plasma and red blood cell generation module bay or the detection of incorrect connector state of the associated dialysate lines of the module may result in an informational message to prompt the user. In either of these two cases, after confirming the informational message, the machine may be allowed to execute a standard hemodialysis therapy without utilization of the specialized blood plasma and red blood cell generation module.

Reference is now made to FIG. 1 which schematically illustrates a blood plasma and red blood cell generation device extracorporeal blood circuit configured for generating blood plasma in accordance with the first embodiment of the system described herein. It should be appreciated that the system of FIG. 1 demonstrates only one example embodiment of the system described herein, and that other possible configurations of the system described herein may be equally or even more suitable, depending on specific requirements. For example, the physical lengths and diameters of blood-tubing comprising the extracorporeal may be interchanged or adjusted, as long as the underlying functionality of the extracorporeal blood circuit remains unchanged.

In the system of FIG. 1 whole blood 101 enters the pre-pump portion of the arterial blood line 102 via blood pump 103 and enters the post-pump portion of the arterial blood line 104. The blood then enters a first plasma dialyzer 105 after passing through blood flow and/or blood pressure monitoring devices (not shown) which send data to a control unit (not shown). The blood is carried by suitable tubing, for example, bloodline tubing made from flexible polyvinylchloride (PVC).

The first specialized dialyzer 105 contains a semipermeable membrane 106 that divides the dialyzer into a blood side component 107 and a dialysate compartment 108. As whole blood 101 passes through blood compartment 107, blood plasma, blood platelets, and other blood constituents (except the red blood cells) traverse the semipermeable membrane 106 and enter the dialysate compartment 108 of the plasma dialyzer. Fresh dialysate or substitution fluid is supplied to the first dialyzer from dialysate line 109, and the blood plasma constituents (denoted 110) exit the first plasma dialyzer 105 via intermediate blood plasma tubing line 111. The blood plasma traverses the semipermeable membrane 106 by diffusion due to a difference in concentration of plasma constituents between blood compartment 107 and dialysate compartment 108 and by convection resultant of the addition of fresh dialysate or substitution fluid from dialysate line 109. The dialyzer cartridge may be of any suitable type plasma dialyzer. For example, such filters include the Evacure and Evaclio plasma separators from LINC medical, the Monet filter from Fresenius Medical Care, and the PlasmaFlo™ from Apheresis Technologies, Inc.

The blood plasma constituents 110 exiting the plasma dialyzer 105 enters intermediate blood plasma tubing line 111 and passes through a restriction valve 112. At the same time, the red blood cells incapable of traversing the semipermeable membrane 106, in along with dialysate or substitution fluid and other whole blood constituents (denoted 113) exit the blood outlet of the plasma dialyzer 105 via venous blood-tubing 114 and are returned to the patient. The restriction valve 115 on venous tubing 114 ensures that the flow rate at the blood outlet of the plasma dialyzer 105 is controlled and is less than the flow rate of whole blood 101 entering the blood inlet of the plasma dialyzer 105. Restriction valve 112 ensures that the flow rate of blood plasma constituents 110 in intermediate blood plasma tubing line 111 does not exceed a desired rate. Additionally, the concurrent restriction action of restriction valve 115 guarantees a minimum flow rate of blood plasma constituents 110 in intermediate blood plasma tubing line 111.

After the blood plasma constituents 110 exit restriction valve 112, this mixture enters a second standard dialyzer 116 containing a semi permeable membrane 117 which divides the second dialyzer 116 into a blood compartment 118 and a dialysate compartment 119.

As the blood plasma constituents 110 pass through blood compartment 118, some of the smaller plasma constituents traverse the semipermeable membrane 117. These plasma constituents, such as uremic toxins, travel across semipermeable membrane 117 by diffusion due to concentration gradient between the blood plasma in blood compartment 118 and dialysate in dialysate compartment 119. Fresh dialysate is supplied to the second dialyzer from dialysate line 120, and spent dialysate is removed from the second dialyzer 116 by dialysate line 121. Alternatively, fresh dialysate may be supplied by dialysate line 121 and spent dialysate may be removed from the second dialyzer 116 by dialysate line 120 to allow for dialysate to run counter-parallel to the blood plasma flow direction. Dialyzed blood plasma constituents 122 exits the second dialyzer 116, enters plasma tubing line 123 and then enters a plasma collection bag 124 with associated blood pressure monitoring devices (not shown) which send this pressure data to a control unit (not shown). An air-permeable filter 125 allows for air, but not fluid, to vacate plasma collection bag 124. Increases in pressure resultant from the plasma collection bag 124 beginning to expand may be detected by the associated blood pressure monitoring devices and result in initiation of a negative feedback loop that reduces the flow rate of whole blood 101 and dialysate (or substitution fluid) from dialysate line 109. As the monitored pressure reaches a desired threshold, restriction valve 112 fully occludes, and the remaining blood constituents are returned to the patient (not shown) through the venous drip chamber 126 of venous tubing 114 and associated blood pressure monitoring devices (not shown) which send this pressure data to a control unit (not shown).

Module bay 127 is indicated to illustrate that such a machine adaptation may be implemented through use of a machine module bay on existing hemodialysis machines such as the 2008T machine by the company Fresenius Medical Care. Implementation of such a module bay may require hydraulic changes, as is discussed in further detail elsewhere herein.

In this way, blood plasma generation is achieved with use of dialysate (or substitution fluid) as blood enters the first plasma dialyzer 105, is separated from the red blood cell constituents of the blood facilitated by the diffusive and convective clearance achieved through use of dialysate fluid. The red blood cell constituents are returned to the patient, while blood plasma concurrently enters a second dialyzer 116 to undergo plasmadiafiltration and is then collected in a plasma collection bag 124.

In an embodiment, the system described herein may enhance current plasmadiafiltration techniques such as those illustrated by the Mars System from Gambro. Plasmadiafiltration is analogous to hemodialysis except that plasma, rather than whole blood, enters into the dialyzer. The dialyzer used may be that of conventional dialysis as it is not the desired for albumin to be able to traverse the semipermeable membrane as is the case for conventional hemodialysis. An advantage of such a technique may be that red-blood cells and other non-plasma constituent may not enter the dialyzer and thus the effective volume and clearance ability may be increased.

Figure 2:
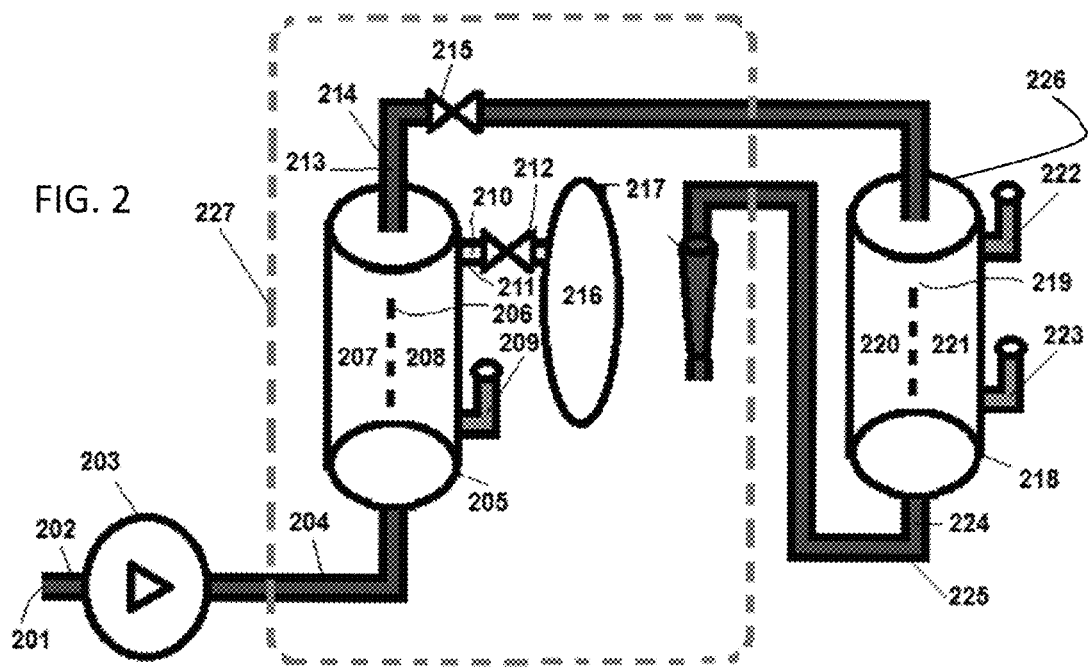
FIG. 2 is a schematic illustration of an extracorporeal blood circuit of a blood plasma and red blood cell generation device configured for generating blood plasma in accordance with a second embodiment of the system described herein.

Reference is now made to FIG. 2 which schematically illustrates a blood plasma and red blood cell generation device with extracorporeal blood circuit configured for generating blood plasma in accordance with the second embodiment of the system described herein. It should be appreciated that the system of FIG. 2 demonstrates only one embodiment of the system described herein, and that other possible configurations of the system described herein may be equally or even more suitable, depending on specific requirements. For example, the physical lengths and diameters of blood-tubing comprising the extracorporeal may be interchanged or adjusted, as long as the underlying functionality of the extracorporeal blood circuit remains unchanged.

In the system of FIG. 2 whole blood 201 enters the pre-pump portion of the arterial blood line 202 via blood pump 203 and enters the post-pump portion of the arterial blood line 204. The blood then enters a first plasma dialyzer 205 after passing through blood flow and/or blood pressure monitoring devices (not shown) which send data to a control unit (not shown). The blood is carried by suitable tubing, for example, bloodline tubing made from flexible polyvinylchloride (PVC).

The first specialized dialyzer 205 contains a semipermeable membrane 206 that divides the dialyzer into a blood side component 207 and a dialysate compartment 208. As whole blood 201 passes through blood compartment 207, blood plasma, blood platelets, and other blood constituents (except the red blood cells) traverse the semipermeable membrane 206 and enter the dialysate compartment 208 of the plasma dialyzer. Fresh dialysate (or substitution fluid) is supplied to the first dialyzer from dialysate line 209, and the blood plasma constituents (denoted 210) exit the first plasma dialyzer 205 via intermediate blood-tubing line 211. The blood plasma traverses the semipermeable membrane 206 by diffusion due to a difference in concentration of plasma constituents between blood compartment 207 and dialysate compartment 208 and by convection resultant of the addition of fresh dialysate or substitution fluid from dialysate line 109. The dialyzer cartridge may be of any suitable type plasma dialyzer. For example, such filters include the Evacure and Evaclio plasma separators from LINC medical, the Monet filter from Fresenius Medical Care, and the PlasmaFlo™ from Apheresis Technologies, Inc.

The blood plasma constituents 210 exiting the plasma dialyzer 205 enters blood plasma tubing line 211 and passes through a restriction valve 212. At the same time, the red blood cells incapable of traversing the semipermeable membrane 206, along with dialysate or substitution fluid and other whole blood constituents (denoted 213) exit the blood outlet of the plasma dialyzer 205 via intermediate blood-tubing line 214. The restriction valve 215 on intermediate blood-tubing line 214 ensures that the flow rate at the blood outlet of the plasma dialyzer 205 is controlled and is less than the flow rate of whole blood 201 entering the blood inlet of the plasma dialyzer 205. Restriction valve 212 ensures that the flow rate of blood plasma constituents 210 in blood plasma tubing line 211 does not exceed a desired rate. Additionally, the concurrent restriction action of restriction valve 215 guarantees a minimum flow rate of blood plasma constituents 210 in blood plasma tubing line 211.

After the blood plasma constituents 210 exit restriction valve 212, this mixture enters a plasma collection bag 216 with associated blood pressure monitoring devices (not shown) which send this pressure data to a control unit (not shown). An air-permeable filter 217 allows for air, but not fluid, to vacate plasma collection bag 216. Increases in pressure resultant from the plasma collection bag 216 beginning to expand may be detected by the associated blood pressure monitoring devices and result in initiation of a negative feedback loop that reduces the flow rate of whole blood 201 and dialysate (or substitution fluid) from dialysate line 209.

After the red blood cell fluid mixture 213 exits the blood outlet of the plasma dialyzer, it then travels through restriction valve 215. After the red blood cell mixture 213 exit restriction valve 215, this mixtures enters a second dialyzer 218 containing a semi permeable membrane 219 which divides the second dialyzer 218 into a blood compartment 220 and a dialysate compartment 221.

As the red blood cell fluid mixture 213 passes through blood compartment 220, some of the smaller remaining red blood cell fluid mixture constituents, such as uremic toxins, traverse the semipermeable membrane 219. These constituents travel across semipermeable membrane 219 by diffusion due to concentration gradient between the red blood cell fluid mixture 213 in blood compartment 220 and dialysate (or substitution fluid) in dialysate compartment 221. Fresh dialysate (or substitution fluid) is supplied to the second dialyzer from dialysate line 222, and spent dialysate is removed from the second dialyzer 218 by dialysate line 223. Alternatively, fresh dialysate may be supplied by dialysate line 223 and spent dialysate may be removed from the second dialyzer 218 by dialysate line 222 to allow for dialysate to run counter-parallel to the red blood cell fluid mixture flow direction. The dialyzed red blood cell fluid mixture 224 exits the second dialyzer 218, and enters venous blood-tubing line 225 and then enters a venous drip chamber 226 with associated blood pressure monitoring devices (not shown) which send this pressure data to a control unit (not shown) and is returned to the patient (not shown).

As the monitored pressure reaches a desired threshold in plasma collection bag 216, restriction valve 212 fully occludes, and the remaining blood constituents are returned to the patient (not shown) through the venous blood chamber 226 via venous tubing 225 and associated blood pressure monitoring devices (not shown) which send this pressure data to a control unit (not shown).

Module bay 227 is indicated to illustrate that such a machine adaptation may be implemented through use of a machine module bay on existing hemodialysis machines such as the 2008T machine by the company Fresenius Medical Care. Implementation of such a module bay may require hydraulic changes, as is discussed in further detail elsewhere herein.

In this way, blood plasma generation is achieved with use of dialysate (or substitution fluid) as blood enters the first plasma dialyzer 205, is separated from the red blood cell constituents of the blood facilitated by the diffusive and convective clearance achieved through use of dialysate fluid. The red blood cell fluid mixture 214 enters a second dialyzer 218 and is then returned to the patient, while blood plasma 210 is concurrently collected in a plasma collection bag 216.

Figure 3:
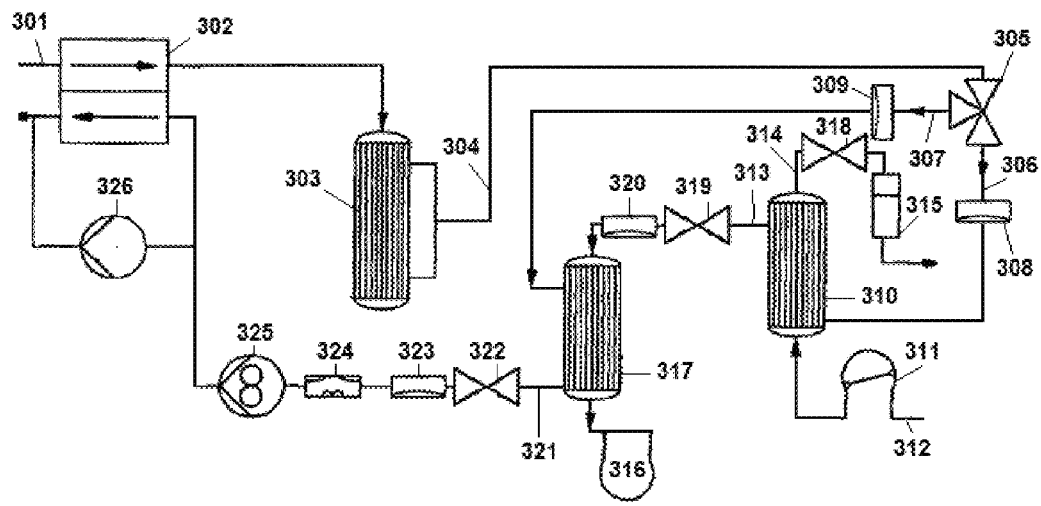
FIG. 3 is a schematic illustration of a blood plasma and red blood cell generation device configured for generating blood plasma in accordance with the first embodiment of the system described herein.

Reference is now made to FIG. 3 which schematically illustrates a blood plasma and red blood cell generation device configured for generating blood plasma in accordance with the first embodiment of the system described herein. The dialysate solution used for the system described herein may be prepared as follows. A suitable quality of water, such as reverse osmosis water, is provided from a water source (not shown). The water enters a water preparation module (not shown) that heats and degasses the water. Any suitable heating and degassing module may be used in conjunction with the system described herein. Examples of such modules are included in the following systems: the Baxter SPS1550, available from Baxter Health Care, Deerfield, Ill.; the Cobe Centry System 3, available from Cobe Labs, Lakewood, Colo.; the Fresenius A2008, available from Fresenius Medical Care, Lexington, Mass.; and the Althin System 1000, available from Althin Medical, Miami, Fla. The degassed, heated water is proportioned with acid and bicarbonate to generate fresh dialysate fluid. The fresh dialysate fluid 301 enters into balancing system 302, to ensure that the inlet and outlet amounts are equal. Examples of such balancing systems can be seen in the 2008 or 4008 by the company Fresenius Medical Care, the machine Centry 3 of company Cobe, the machine System 1000 of company Althin Medical, the machine MIRO-CLAV of company Baxter, or the machine DIALOG of company B. Braun-Melsungen.

The fresh dialysate fluid 301 from the balancing system 302 passes through a conductivity and temperature monitor (not shown) which prevent incorrect dialysate fluid composition and/or temperature from reaching the patient, and then through a first sterile filter 303 comprising a semipermeable membrane. Examples of such filters include the Diasafe Plus Filter by Fresenius Medical Care.

The dialysis fluid passes through the membrane of the sterile filter 303 to a line 304 for producing a cleansed dialysate fluid. The cleansed dialysate fluid enters into three-way valve 305. Three-way valve 305 proportions the cleansed dialysate fluid, through use of software-duty cycling. Through use of duty-cycling of valves, or in other words toggling the valves off and on at known rates, a total amount of cleansed dialysate fluid can be accurately partitioned to a first dialysate line 306, and a second dialysate line 307. It should be appreciated that a three-way valve is described; however, two individual valves may also be used if desired.

A fraction of the dialysate fluid travels through both line 306 and 307 concurrently. The first dialysate line 306 and second dialysate line 307 each have an associated pressure transducer 308 and 309 to assist with monitoring of pressure in dialysate lines 306 and 307. Cleansed dialysate fluid from the first line 306 enters the dialysate inlet of the plasma dialyzer 310.

The extracorporeal circuit comprises a blood pump 311, an arterial tube system 312, the blood portion of the plasma dialyzer 310, an intermediate blood plasma tubing line 313, a venous blood-tubing 314 incorporating the venous drip chamber 315, and a plasma collection bag 316. Additionally, the extracorporeal circuit comprises a second dialyzer 317, restriction valves 318 and 319 which ensure appropriate flow rates of the blood plasma fluid and red blood cell mixture exiting the plasma dialyzer 310, and an optional pressure sensor 320.

Blood enters the blood inlet of the plasma dialyzer 310. Plasma traverses the semipermeable membrane of the plasma dialyzer 310 facilitated by the introduction of cleansed dialysate fluid into the plasma dialyzer 310 via dialysate line 306. Red blood cells incapable of traversing the semipermeable membrane along with dialysate fluid and other whole blood constituents exit the blood outlet of the plasma dialyzer 310 via venous blood-tubing 314. The red blood cell mixture passes a restriction valve 318, enters a venous drip chamber 315, and then is returned to the patient (not shown). Restriction valve 318 ensures that the flow rate of whole blood into the plasma dialyzer 310 is greater than the flow rate of the red blood cell mixture exiting the blood outlet of the plasma dialyzer 310.

Separated blood plasma constituents exit the dialysate port outlet of the plasma dialyzer 310 through intermediate blood plasma tubing line 313, and passes through restriction valve 319 which ensures the flow rate of the blood plasma constituents does not exceed a desired threshold. Additionally, the restriction valves 319 together with restriction valve 318 ensure minimum flow rates at the blood outlet and dialysate outlet of the plasma dialyzer 310. The blood plasma constituents then travel through an optional pressure sensor 320. Optional pressure sensor 320 allows for pressure monitoring in intermediate blood plasma tubing 313. After traversing the intermediate blood plasma tubing 313, the blood plasma constituents enters into a second dialyzer 317.

Blood plasma constituents enter the blood inlet of a second dialyzer 317, and cleansed blood plasma exits the blood outlet of the second dialyzer 317 and enters into a plasma collection bag 316 with an air-permeable filter (not shown) to allow for air to vacate the plasma collection bag as cleansed blood plasma enters the plasma collection bag 316.

Fresh dialysate from line 307 passes through a pressure sensor 309 and enters into the second dialyzer 317. Duty-cycling of the fresh dialysate valves (valve 305) allow the amount of fresh dialysate supplied to the first dialyzer 310 and second dialyzer 317 to be controlled. Fresh dialysate facilitates diffusion of smaller plasma constituents, such as uremic toxins, into the dialysate compartment of the second dialyzer 317. Spent dialysate fluid leaves the second dialyzer 317 through a spent dialysate line 321, and passes through a spent dialysate valve 322, a dialysate pressure monitor 323, and a blood leak detector 324. The spent dialysate passes through the balancing system 302 by means of a dialysate circulation pump 325 and further to the drain (not shown). After passing through blood leak detector 324, the spent dialysate enters an air separation chamber (not shown), which makes possible the separation of air, since many balancing systems are disturbed by air. Parallel to the balancing system 302 there is a UF Pump 326 to remove ultrafiltrate.

In this way, blood plasma generation is achieved as blood plasma is separated from whole blood through traversal through the first plasma dialyzer 310 with enhanced convective and diffusive mass transport of blood plasma constituents resultant of the use of dialysate fluid. Blood plasma is separated from the red blood cell constituents of the blood, enters into a second dialyzer 317, and is collected in a plasma collection bag 316. The red blood cell constituents along with dialysate are returned to the patient with real-time monitoring of venous pressure and level detector monitoring for detecting air.

Figure 4:
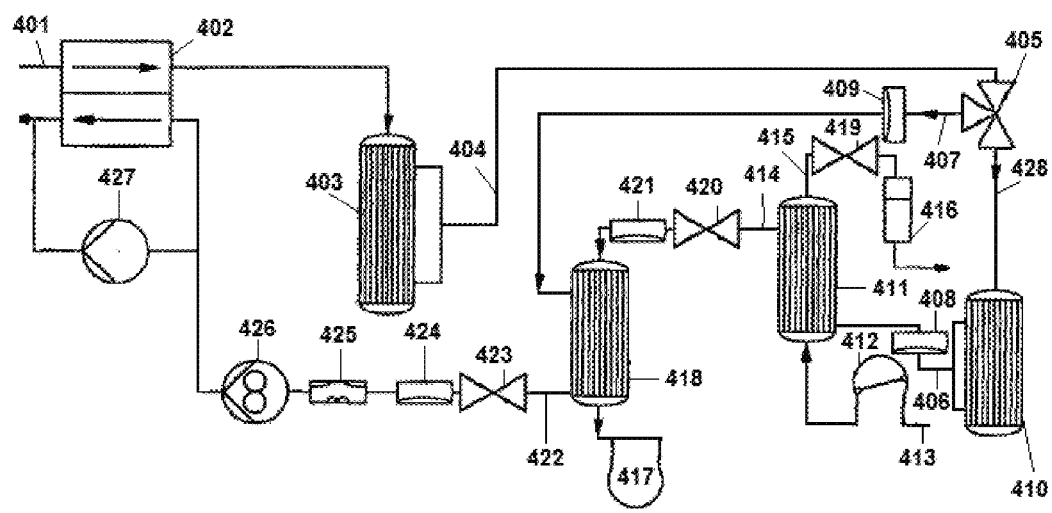
FIG. 4 is schematic illustration of a blood plasma and red blood cell generation device configured for generating blood plasma in accordance with the first embodiment of the system described herein with an additional filter in accordance with an optional modality of the first embodiment.

Reference is now made to FIG. 4 which schematically illustrates a blood plasma and red blood cell generation device configured for generating blood plasma in accordance with the first embodiment of the system described herein with an additional filter in accordance with an optional modality of the first embodiment of the system described herein.

The fresh dialysate fluid 401 from the balancing system 402 passes through a conductivity and temperature monitor (not shown), and then through a first sterile filter 403 comprising a semipermeable membrane. Examples of such filters include the Diasafe Plus Filter by Fresenius Medical Care.

Cleansed dialysate fluid passes through line 404. The cleansed dialysate fluid enters into three-way valve 405 which accurately partitioned the cleansed dialysate fluid to a first dialysate line 406 and toward a second dialysate line 407 (via line 428) through duty-cycling of three-way valve 405. The first dialysate line 406 and second dialysate line 407 each have an associated pressure transducer 408 and 409 to assist with monitoring of pressure in dialysate lines 406 and 407.

In the modality of the first embodiment of the system described herein, cleansed dialysate fluid from line 428 enters a second sterile filter 410. Preparation of a sterile substitution fluid is performed by filtration of a dialysate across at least two filter membranes with a molecular weight cut-off of not more than 40,000 Daltons; however, smaller molecular weight cut-offs approaching 5,000 Daltons can be used. In this way, substitution fluid, rather than dialysate fluid, enters into the dialysate inlet of the plasma dialyzer 411 via dialysate line 406.

The extracorporeal circuit, in an analogous way to that of FIG. 3, comprises a blood pump 412, an arterial tube system 413, the blood portion of the plasma dialyzer 411, an intermediate blood plasma tubing line 414, a venous blood-tubing 415 incorporating the venous drip chamber 416, and a plasma collection bag 417. Additionally, the extracorporeal circuit comprises a second dialyzer 418, restriction valves 419 and 420 which ensure appropriate flow rates of the blood plasma fluid and red blood cell mixture exiting the plasma dialyzer 411, and an optional pressure sensor 421.

Blood enters the blood inlet of the plasma dialyzer 410. Plasma traverses the semipermeable membrane of the plasma dialyzer 410 facilitated by the introduction of substitution fluid into the plasma dialyzer 410 via dialysate line 406. Plasma exits into intermediate blood plasma tubing line 414. Red blood cells exit the blood outlet of the plasma dialyzer 411 via venous blood-tubing 415. The red blood cell mixture passes a restriction valve 419, enters a venous drip chamber 416, and then is returned to the patient (not shown).

Blood plasma constituents in the intermediate blood plasma tubing line 414 pass through restriction valve 420 and optional pressure sensor 421, and then enter into a second dialyzer 418. Cleansed blood plasma exits the blood outlet of the second dialyzer 418 and enters into a plasma collection bag 417 with an air-permeable filter (not shown) to allow for air to vacate the plasma collection bag 417.

Fresh dialysate from line 407 passes through a pressure sensor 409 and enters into the second dialyzer 418. Duty-cycling of the fresh dialysate valves (valve 405) allow the amount of fresh dialysate supplied to the first dialyzer 411 and second dialyzer 418 to be controlled. Spent dialysate fluid leaves the second dialyzer 418 through spent dialysate line 422, and passes through a spent dialysate valve 423, a dialysate pressure monitor 424, and a blood leak detector 425. The spent dialysate passes through the balancing system 402 by means of a dialysate circulation pump 426 and further to the drain (not shown). After passing through blood leak detector 425, the spent dialysate enters an air separation chamber (not shown). Parallel to the balancing system 402 there is a UF Pump 427 to remove ultrafiltrate.

In this way, blood plasma generation is achieved with use of sterile substitution fluid as blood enters the first plasma dialyzer 411, is separated from the red blood cell constituents of the blood facilitated by the diffusive and convective clearance achieved through use of the sterile substitution fluid. The red blood cell constituents are returned to the patient, while blood plasma concurrently enters a second dialyzer 418, and is collected in a plasma collection bag 417.

Figure 5:
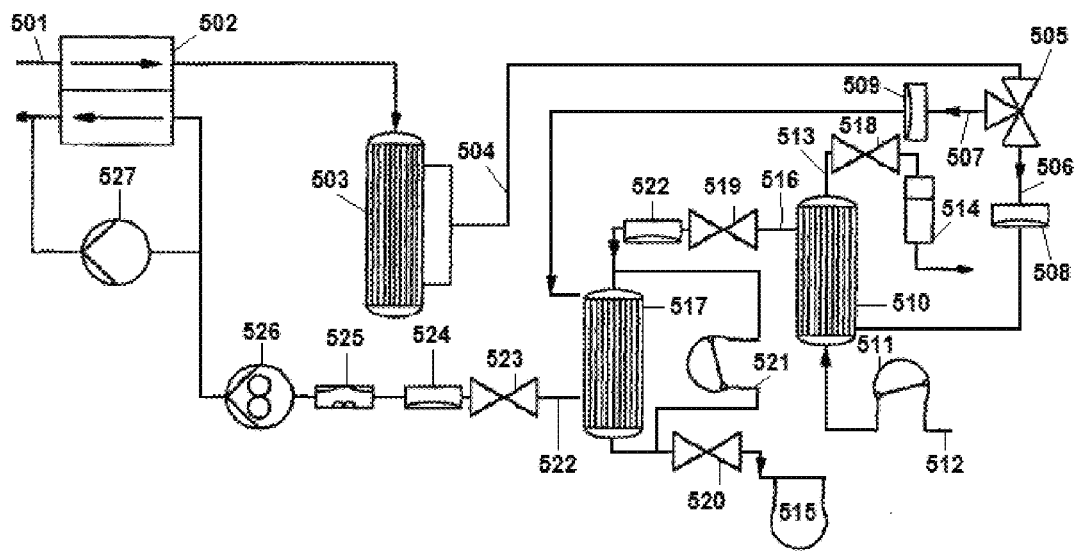
FIG. 5 is schematic illustration of a blood plasma and red blood cell generation device configured for generating blood plasma in accordance with the first embodiment of the system described herein with a recirculation loop in accordance with an optional modality of the first embodiment.

Reference is now made to FIG. 5 which schematically illustrates a blood plasma and red blood cell generation device configured for generating blood plasma in accordance with the first embodiment of the system described herein with a recirculation loop in accordance with an optional modality of the first embodiment of the system described herein.

The fresh dialysate fluid 501 from the balancing system 502 passes through a conductivity and temperature monitor (not shown), and then through a first sterile filter 503 comprising a semipermeable membrane. Examples of such filters include the Diasafe Plus Filter by Fresenius Medical Care.

Cleansed dialysate fluid passes through line 504. The cleansed dialysate fluid enters into three-way valve 505 which accurately partitioned the cleansed dialysate fluid to a first dialysate line 506 and a second dialysate line 507 through duty-cycling of three-way valve 505. The first dialysate line 506 and second dialysate line 507 each have an associated pressure transducer 508 and 509 to assist with monitoring of pressure in dialysate lines 506 and 507. Cleansed dialysate fluid from the first line 506 enters the dialysate inlet of the plasma dialyzer 510.

The extracorporeal circuit, in an analogous way to FIGS. 3 and 4, comprises a blood pump 511, an arterial tube system 512, the blood portion of the plasma dialyzer 510, a venous blood-tubing 513 incorporating the venous drip chamber 514, and a plasma collection bag 515. Additionally, the extracorporeal circuit includes a specialized intermediate blood plasma tubing line 516 (particular to this optional modality of the first embodiment of the system described herein), a second dialyzer 517, restriction valves 518 and 519 which ensure appropriate flow rates of the blood plasma fluid and red blood cell mixture exiting the plasma dialyzer, a recirculation valve 520, a recirculation pump 521, and an optional pressure sensor 522.

Blood enters the blood inlet of the plasma dialyzer 510. Plasma traverses the semipermeable membrane of the plasma dialyzer 510 facilitated by the introduction of dialysate fluid into the plasma dialyzer 510 via dialysate line 506. Plasma exits into intermediate blood plasma tubing line 516. Red blood cells exit the blood outlet of the plasma dialyzer 510 via venous blood-tubing 513. The red blood cell mixture passes a restriction valve 518, enters a venous drip chamber 514, and then is returned to the patient (not shown).

Blood plasma constituents in the intermediate blood plasma tubing line 516 pass through restriction valve 519 and optional pressure sensor 522, and then enter into a second dialyzer 517. Cleansed blood plasma exits the blood outlet of the second dialyzer 517, passes through a recirculation valve 520, and then enters into a plasma collection bag 515 with an air-permeable filter (not shown) to allow for air to vacate the plasma collection bag 515. Recirculation pump 521 remains off when cleansed blood plasma fluid enters into blood plasma collection bag 515. When cleansed blood plasma is not being collected, recirculation pump 521 turns on, restriction valve 520 closes, and cleansed blood plasma is recirculated through the second dialyzer 517. In this manner, blood plasma becomes further cleansed resulting in non-continuous delivery of multi-filtered, cleansed blood plasma in plasma collection bag 515. Additionally, when cleansed blood is not being collected, blood pump 515 remains off and fresh dialysate line 506 is not supplied with dialysate through control of three-way valve 505.

It should be appreciated, however, that fresh dialysate line 506 may be supplied with a reduced amount of dialysate with concurrent operation of blood pump 515 at a reduced rate to allow for continuous delivery of multi-filtered, cleansed blood plasma into collection bag 515. In this case, valve 520 may periodically open to allow fluid to enter plasma collection bag 515 at a rate equal to the flow rate of plasma exiting plasma dialyzer 510.

Fresh dialysate from line 507 passes through a pressure sensor 509 and enters into the second dialyzer 517. Duty-cycling of the fresh dialysate valves (valve 505) allow the amount of fresh dialysate supplied to the first dialyzer 510 and second dialyzer 517 to be controlled. Spent dialysate fluid leaves the second dialyzer 517 through spent dialysate line 522, and passes through a spent dialysate valve 523, a dialysate pressure monitor 524, and a blood leak detector 525. The spent dialysate passes through the balancing system 502 by means of a dialysate circulation pump 526 and further to the drain (not shown). After passing through blood leak detector 525, the spent dialysate enters an air separation chamber (not shown). Parallel to the balancing system 502 there is a UF Pump 527 to remove ultrafiltrate.

In this way, blood plasma generation is achieved as blood enters the first plasma dialyzer 510, is separated from the red blood cell constituents of the blood facilitated by the diffusive and convective clearance achieved through use of dialysate fluid. The red blood cell constituents are returned to the patient, while blood plasma enters a second dialyzer 517, and is collected in a plasma collection bag 515.

Figure 6:
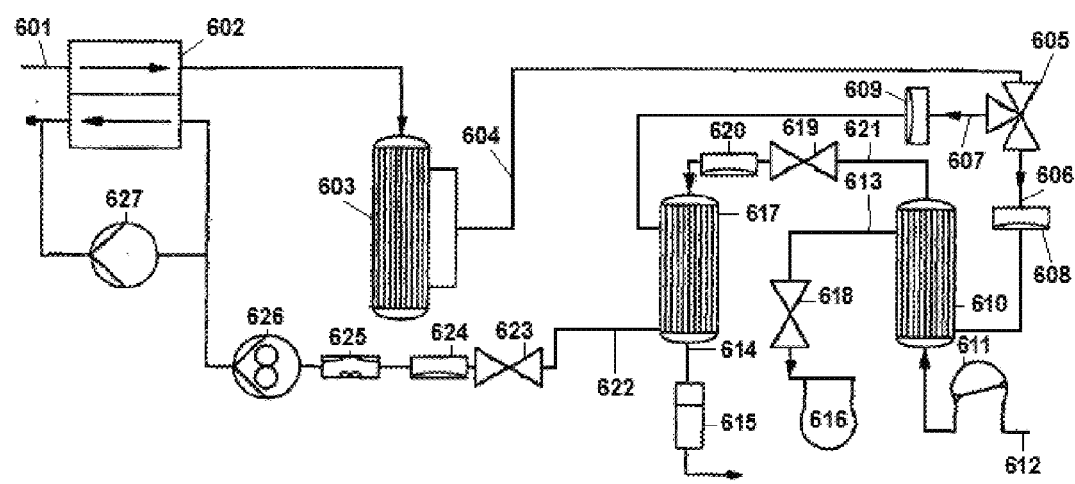
FIG. 6 is schematic illustration of a blood plasma and red blood cell generation device configured for generating blood plasma in accordance with the second embodiment of the system described herein.

Reference is now made to FIG. 6 which schematically illustrates a blood plasma and red blood cell generation device configured for generating blood plasma in accordance with the second embodiment of the system described herein.

The fresh dialysate fluid 601 from the balancing system 602 passes through a conductivity and temperature monitor (not shown), and then through a first sterile filter 603 comprising a semipermeable membrane. Examples of such filters include the Diasafe Plus Filter by Fresenius Medical Care.

Cleansed dialysate fluid passes through line 604. The cleansed dialysate fluid enters into three-way valve 605 which accurately partitioned the cleansed dialysate fluid to a first dialysate line 606 and toward a second dialysate line 607 through duty-cycling of three-way valve 605. The first dialysate line 606 and second dialysate line 607 each have an associated pressure transducer 608 and 609 to assist with monitoring of pressure in dialysate lines 606 and 607. Cleansed dialysate fluid from the first line 606 enters the dialysate inlet of the plasma dialyzer 610.

The extracorporeal circuit comprises a blood pump 611, an arterial tube system 612, the blood portion of the plasma dialyzer 610, an intermediate blood plasma tubing line 613, a venous blood-tubing 614 incorporating the venous drip chamber 615, and a plasma collection bag 616. Additionally, the extracorporeal circuit comprises a second dialyzer 617, restriction valves 618 and 619 which ensure appropriate flow rates of the blood plasma fluid and red blood cell mixture exiting the plasma dialyzer 610, intermediate red blood cell line 621 and an optional pressure sensor 620.

Blood enters the blood inlet of the plasma dialyzer 610. Plasma traverses the semipermeable membrane of the plasma dialyzer 610 facilitated by the introduction of cleansed dialysate fluid into the plasma dialyzer 610 via dialysate line 606. Red blood cells incapable of traversing the semipermeable membrane along with dialysate fluid and other whole blood constituents exit the blood outlet of the plasma dialyzer 610 into the intermediate red blood cell line 621. The red blood cell mixture passes a restriction valve 619 and optional pressure sensor 620. The Red blood cell mixture enter the blood inlet of a second dialyzer 617, and a cleansed red blood cell mixture exits the blood outlet of the second dialyzer 617 and enters a venous drip chamber 615, and then is returned to the patient (not shown). Restriction valve 619 ensures that the flow rate of whole blood into the plasma dialyzer 610 is greater than the flow rate of the red blood cell mixture exiting the blood outlet of the plasma dialyzer 610.

Separated blood plasma constituents exit the dialysate port outlet of the plasma dialyzer 610 through intermediate blood plasma tubing line 613, and passes through restriction valve 618 which ensures the flow rate of the blood plasma constituents does not exceed a desired threshold. Additionally, the restriction valves 619 together with restriction valve 618 ensure minimum flow rates at the blood outlet and dialysate outlet of the plasma dialyzer 610. After traversing the intermediate blood plasma tubing 613, the blood plasma constituents enters into plasma collection bag 616 with an air-permeable filter (not shown) to allow for air to vacate the plasma collection bag as blood plasma enters the plasma collection bag 616.

Fresh dialysate from line 607 passes through a pressure sensor 609 and enters into the second dialyzer 617. Duty-cycling of the fresh dialysate valves (valve 605) allow the amount of fresh dialysate supplied to the first dialyzer 610 and second dialyzer 617 to be controlled. Fresh dialysate facilitates diffusion of smaller constituents of the red blood cell mixture, such as uremic toxins, into the dialysate compartment of the second dialyzer 617. Spent dialysate fluid leaves the second dialyzer 617 through a spent dialysate line 622, and passes through a spent dialysate valve 623, a dialysate pressure monitor 624, and a blood leak detector 625. The spent dialysate passes through the balancing system 602 by means of a dialysate circulation pump 626 and further to the drain (not shown). After passing through blood leak detector 625, the spent dialysate enters an air separation chamber (not shown), which makes possible the separation of air, since many balancing systems are disturbed by air. Parallel to the balancing system 602 there is a UF Pump 627 to remove ultrafiltrate.

In this way, blood plasma generation is achieved as blood plasma is separated from whole blood through traversal through the first plasma dialyzer 610 with enhanced convective and diffusive mass transport of blood plasma constituents resultant of the use of dialysate fluid. A Red blood cell mixture is separated from the blood plasma constituents of the blood, enters into a second dialyzer 617, and is returned to the patient. The blood plasma is collected in plasma collection bag 616.

Figure 7:
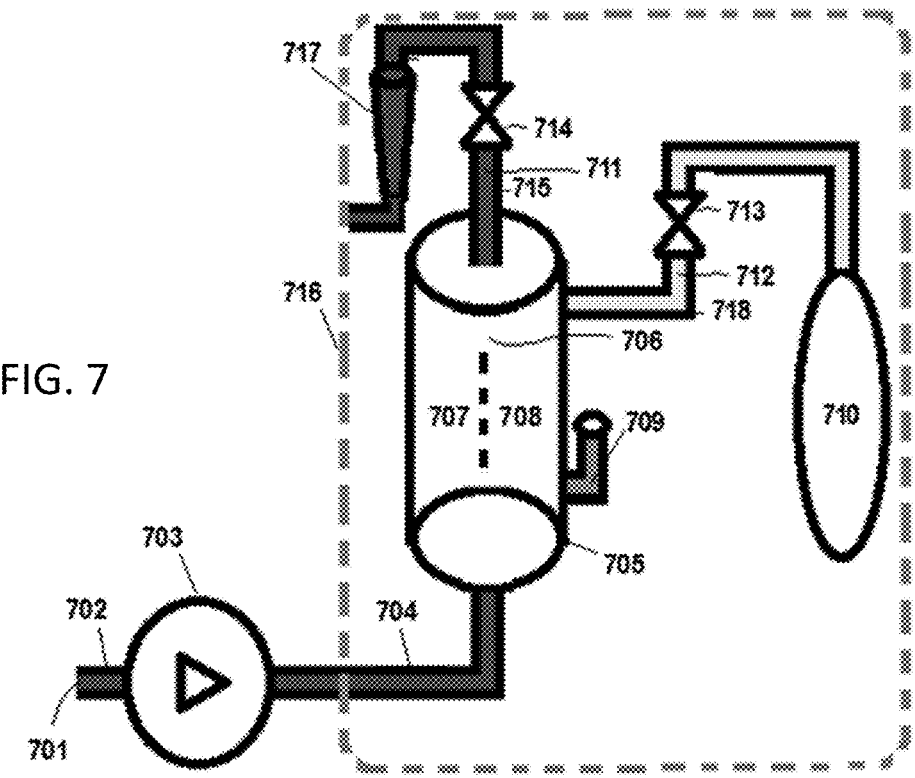
FIG. 7 is a schematic illustration of an extracorporeal blood circuit of a blood plasma and red blood cell generation device configured for generating blood plasma in accordance with a third embodiment of the system described herein.

Reference is now made to FIG. 7 which schematically illustrates a blood plasma and red blood cell generation device extracorporeal blood circuit configured for generating blood plasma in accordance with the third embodiment of the system described herein. It should be appreciated that the system of FIG. 7 demonstrates only one embodiment of the system described herein, and that other possible configurations of the system described herein may be equally or even more suitable, depending on specific requirements. For example, the physical lengths and diameters of blood-tubing comprising the extracorporeal may be interchanged or adjusted, as long as the underlying functionality of the extracorporeal blood circuit remains unchanged.

In the system of FIG. 7 whole blood 701 enters the pre-pump portion of the arterial blood line 702 via blood pump 703 and enters the post-pump portion of the arterial blood line 704. The blood then enters a first plasma dialyzer 705 after passing through blood flow and/or blood pressure monitoring devices (not shown) which send data to a control unit (not shown). The blood is carried by suitable tubing, for example, bloodline tubing made from flexible polyvinylchloride (PVC).

The specialized dialyzer 705 contains a semipermeable membrane 706 that divides the dialyzer into a blood side component 707 and a dialysate compartment 808. As whole blood 701 passes through blood compartment 707, blood plasma, blood platelets, and other blood constituents (except the red blood cells) traverse the semipermeable membrane 706 and enter the dialysate compartment 708 of the plasma dialyzer. Fresh dialysate or substitution fluid is supplied to the dialyzer from dialysate line 709, and the blood plasma constituents (denoted 712) exit the first plasma dialyzer 705 via intermediate blood-tubing line 718. The blood plasma traverses the semipermeable membrane 706 by diffusion due to a difference in concentration of plasma constituents between blood compartment 707 and dialysate compartment 708 and by convection resultant of the addition of fresh dialysate or substitution fluid from dialysate line 709. The dialyzer cartridge may be of any suitable type plasma dialyzer. For example, such filters include the Evacure and Evaclio plasma separators from LINC medical, the Monet filter from Fresenius Medical Care, and the PlasmaFlo™ from Apheresis Technologies, Inc.

The blood plasma constituents 712 exiting the plasma dialyzer 705 enters blood plasma tubing line 718 and passes through a restriction valve 713. At the same time, the red blood cells incapable of traversing the semipermeable membrane 706, along with dialysate or substitution fluid and other whole blood constituents (denoted 711) exit the blood outlet of the plasma dialyzer 705 via venous blood-tubing line 715. The restriction valve 714 on venous blood-tubing line 715 ensures that the flow rate at the blood outlet of the plasma dialyzer 705 is controlled and is less than the flow rate of whole blood 701 entering the blood inlet of the plasma dialyzer 705. Restriction valve 713 ensures that the flow rate of blood plasma constituents 712 in blood plasma tubing line 718 does not exceed a desired rate. Additionally, the concurrent restriction action of restriction valve 714 guarantees a minimum flow rate of blood plasma constituents 712 in blood plasma tubing line 718.

After the blood plasma constituents 712 exit restriction valve 713, this mixture enters a plasma collection bag chamber 710 with associated blood pressure monitoring devices (not shown) which send this pressure data to a control unit (not shown). An air-permeable filter (not shown) allows for air, but not fluid, to vacate plasma collection bag 710. Increases in pressure resultant from the plasma collection bag 710 beginning to expand may be detected by the associated blood pressure monitoring devices and result in initiation of a negative feedback loop that reduces the flow rate of whole blood 701 and dialysate (or substitution fluid) from dialysate line 709.

After the red blood cell fluid mixture 713 exits the blood outlet of the plasma dialyzer, it then travels through restriction valve 714 and enters venous blood-tubing line 715 and then enters a venous drip chamber 717 with associated blood pressure monitoring devices (not shown) which send this pressure data to a control unit (not shown) and is returned to the patient (not shown).

As the monitored pressure reaches a desired threshold in plasma collection bag 710, restriction valve 713 fully occludes, and the remaining blood constituents are returned to the patient (not shown) through the venous blood chamber 717 of venous blood-tubing 715 and associated blood pressure monitoring devices (not shown) which send this pressure data to a control unit (not shown).

Module bay 716 is indicated to illustrate that such a machine adaptation may be implemented through use of a machine module bay on existing hemodialysis machines. Implementation of such a module bay may require hydraulic changes, as is discussed in further detail elsewhere herein.

In this way, blood plasma generation is achieved as blood plasma is separated from whole blood through traversal through the first plasma dialyzer 705 with enhanced convective and diffusive mass transport of blood plasma constituents resultant of the use of dialysate or substitution fluid. A Red blood cell mixture is separated from the blood plasma constituents of the blood, and is returned to the patient. The blood plasma is collected in plasma collection bag 710.

Figure 8:
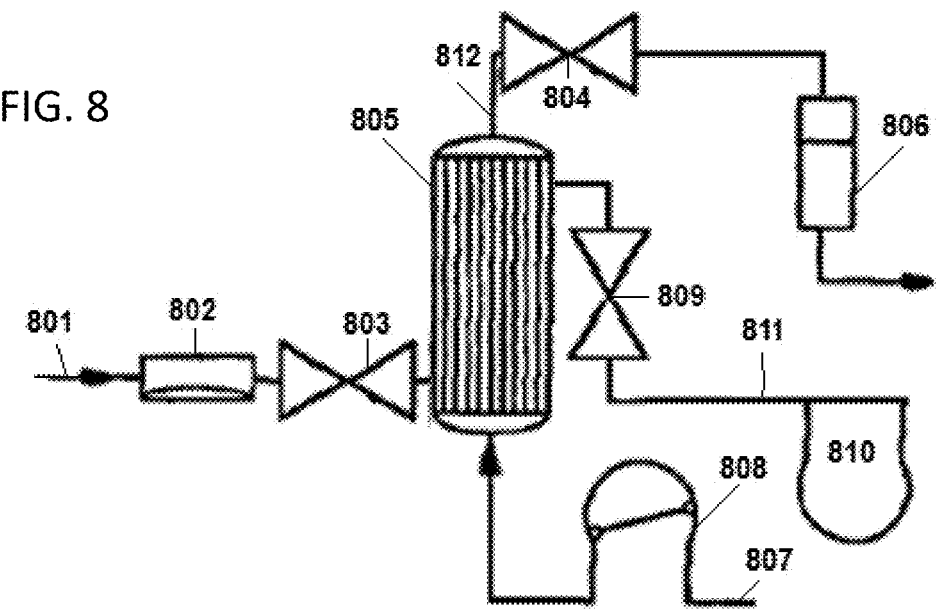
FIG. 8 is schematic illustration of a blood plasma and red blood cell generation device configured for generating blood plasma in accordance with the third embodiment of the system described herein.

Reference is now made to FIG. 8 which schematically illustrates a blood plasma and red blood cell generation device configured for generating blood plasma in accordance with the third embodiment of the system described herein. The dialysate solution used for the system described herein may be prepared as follows. A suitable quality of water, such as reverse osmosis water, is provided from a water source (not shown). The water enters a water preparation module (not shown) that heats and degasses the water. Any suitable heating and degassing module may be used in conjunction with the system described herein. The degassed, heated water is proportioned with acid and bicarbonate to generate fresh dialysate fluid. The fresh dialysate fluid 801 passes through a conductivity and temperature monitor (not shown) which prevent incorrect dialysate fluid composition and/or temperature from reaching the patient, and then through a first sterile filter (not shown) comprising a semipermeable membrane producing cleansed dialysate and then optionally through a second sterile filter (not shown) comprising a semipermeable membrane producing substitution fluid. The cleansed dialysate or substitution fluid then passes through an associated pressure transducer 802 and then passes through bypass valve 803. After passing through bypass valve 803, the cleansed dialysate or substitution fluid enters the dialysate inlet of the plasma dialyzer 805.

The extracorporeal circuit comprises a blood pump 808, an arterial tube system 807, the blood portion of the plasma dialyzer 805, an intermediate blood plasma tubing line 811, a venous blood-tubing 812 incorporating the venous drip chamber 806, and a plasma collection bag 810. Additionally, the extracorporeal circuit comprises restriction valves 809 and 804 which ensure appropriate flow rates of the blood plasma fluid and red blood cell mixture exiting the plasma dialyzer 805.

Blood enters the blood inlet of the plasma dialyzer 805 and traverses the semipermeable membrane facilitated by the introduction of cleansed dialysate fluid or substitution fluid. Red blood cells incapable of traversing the semipermeable membrane along with dialysate fluid and other whole blood constituents exit the blood outlet of the plasma dialyzer 805 via venous blood-tubing 812. The red blood cell mixture passes a restriction valve 804, enters a venous drip chamber 806, and then is returned to the patient (not shown). Restriction valve 804 ensures that the flow rate of whole blood into the plasma dialyzer 805 is greater than the flow rate of the red blood cell mixture exiting the blood outlet of the plasma dialyzer 805.

Separated blood plasma constituents exit the dialysate port outlet of the plasma dialyzer 805 through intermediate blood plasma tubing line 811, and passes through restriction valve 809 which ensures the flow rate of the blood plasma constituents does not exceed a desired threshold and enters into a plasma collection bag 810 with an air-permeable filter (not shown) to allow for air to vacate the plasma collection bag as blood plasma enters the plasma collection bag 810. Additionally, the restriction valves 809 together with restriction valve 804 ensure minimum flow rates at the blood outlet and dialysate outlet of the plasma dialyzer 805.

In this way, blood plasma generation is achieved as blood plasma is separated from whole blood through traversal through the first plasma dialyzer 805 with enhanced convective and diffusive mass transport of blood plasma constituents resultant of the use of dialysate or substitution fluid. Blood plasma is separated from the red blood cell constituents of the blood and is collected in a plasma collection bag 810. The red blood cell constituents along with dialysate (or substitution fluid) are returned to the patient with real-time monitoring of venous pressure and level detector monitoring for detecting air.

Reference is now made to FIG. 9 which schematically illustrates a blood plasma and red blood cell generation device extracorporeal blood circuit configured for generating blood plasma in accordance with the fourth embodiment of the system described herein. It should be appreciated that the system of FIG. 9 demonstrates only one embodiment of the system described herein, and that other possible configurations of the system described herein may be equally or even more suitable, depending on specific requirements.

For example, the extracorporeal circuit may be configured in a way such that the red blood cell mixture exiting the plasma dialyzer is recirculated through a second dialyzer and collected instead of blood plasma; however, unlike the other embodiments of the system described herein it may be less desirable to collect red blood cells instead of blood plasma resultant of the concurrent hemodialysis therapy as this embodiment may be intended for blood component collection from an individual such as a dialysis patient whom likely has some degree of renal failure and as a result may not be capable of losing a significant amount of red blood cells.

In the system of FIG. 9 whole blood 901 enters the pre-pump portion of the arterial blood line 902 via blood pump 903 and enters the post-pump portion of the arterial blood line 904. A portion of the blood passes through valve 905, which is duty-cycled to allow a fraction of the whole blood to enter a first plasma dialyzer 906 after passing through blood flow and/or blood pressure monitoring devices (not shown) which send data to a control unit (not shown). The blood is carried by suitable tubing, for example, bloodline tubing made from flexible polyvinylchloride (PVC).

The first specialized dialyzer 906 contains a semipermeable membrane 909 that divides the dialyzer into a blood side component 907 and a dialysate compartment 908. As whole blood 901 passes through blood compartment 907, blood plasma, blood platelets, and other blood constituents (except the red blood cells) traverse the semipermeable membrane 909 and enter the dialysate compartment 908 of the plasma dialyzer. Fresh dialysate or substitution fluid is supplied to the first dialyzer from dialysate line 919, and the blood plasma constituents (denoted 910) exit the first plasma dialyzer 906 via intermediate blood-tubing line 911. The blood plasma traverses the semipermeable membrane 909 by diffusion due to a difference in concentration of plasma constituents between blood compartment 907 and dialysate compartment 908 and by convection resultant of the addition of fresh dialysate or substitution fluid from dialysate line 919. The dialyzer cartridge may be of any suitable type plasma dialyzer.

The blood plasma constituents 910 exiting the plasma dialyzer 906 enters blood plasma tubing line 911 and passes through a restriction valve 912. At the same time, the red blood cells incapable of traversing the semipermeable membrane 909, along with dialysate or substitution fluid and other whole blood constituents (denoted 914) exit the blood outlet of the plasma dialyzer 906 via intermediate blood-tubing line 934. The restriction valve 915 on intermediate blood-tubing line 934 ensures that the flow rate at the blood outlet of the plasma dialyzer 906 is controlled and is less than the flow rate of whole blood 901 entering the blood inlet of the plasma dialyzer 906. Restriction valve 912 ensures that the flow rate of blood plasma constituents 910 in blood plasma tubing line 911 does not exceed a desired rate. Additionally, the concurrent restriction action of restriction valve 915 guarantees a minimum flow rate of blood plasma constituents 910 in blood plasma tubing line 911.

After the blood plasma constituents 910 exit restriction valve 912, this mixture enters a second standard dialyzer 920 containing a semi permeable membrane 923 which divides the second dialyzer into blood compartment 921 and dialysate compartment 922. As the blood plasma constituents 910 pass through blood compartment 921, some of the smaller plasma constituents traverse the semipermeable membrane 923. These plasma constituents, such as uremic toxins, travel across semipermeable membrane 923 by diffusion due to concentration gradient between the blood plasma in blood compartment 921 and dialysate in dialysate compartment 922. Fresh dialysate is supplied to the second dialyzer from dialysate line 917, and spent dialysate is removed from the second dialyzer 920 by dialysate line 918. Alternatively, fresh dialysate may be supplied by dialysate line 918 and spent dialysate may be removed from the second dialyzer 920 by dialysate line 917 to allow for dialysate to run counter-parallel to the blood plasma flow direction. Dialyzed blood plasma constituents 924 exits the second dialyzer 920, and enters plasma tubing line 935. Recirculation pump 925 remains off when cleansed blood plasma fluid 924 passes valve 926 and enters into blood plasma collection bag 927. When cleansed blood plasma is not being collected, recirculation pump 925 turns on, valve 926 closes, and cleansed blood plasma is recirculated through the second dialyzer 920. In this manner, blood plasma becomes further cleansed resulting in non-continuous delivery of multi-filtered, cleansed blood plasma in plasma collection bag 925.

While plasma is being cleansed by second dialyzer 920, the remaining portion of the whole blood 901 enters a third dialyzer 936 containing a semipermeable membrane 928 which divides the dialyzer into blood compartment 929 and dialysate compartment 930. As the remaining portion of the whole blood 901 passes through blood compartment 929, typical hemodialysis occurs allowing for uremic toxins to traverse the semipermeable membrane 929. These uremic toxins travel across semipermeable membrane 929 by diffusion due to concentration gradient between the blood plasma in blood compartment 929 and dialysate in dialysate compartment 930. Fresh dialysate is supplied to the third dialyzer 936 from dialysate line 931, and spent dialysate is removed from the third dialyzer 936 by dialysate line 932. Alternatively, fresh dialysate may be supplied by dialysate line 932 and spent dialysate may be removed from the third dialyzer 936 by dialysate line 931 to allow for dialysate to run counter-parallel to the blood flow direction. Dialyzed blood 916 exits the third dialyzer 936 and enter intermediate blood-tubing line 934. The dialyzed blood 916 combines with the dialysate or substitution fluid and other whole blood constituents 914 and enters venous drip chamber 933 and is returned to the patient (not shown).

The plasma collection bag chamber 927 with associated blood pressure monitoring devices (not shown) sends pressure data to a control unit (not shown). An air-permeable filter (not shown) allows for air, but not fluid, to vacate plasma collection bag 927. Increases in pressure resultant from the plasma collection bag 927 beginning to expand may be detected by the associated blood pressure monitoring devices and result in initiation of a negative feedback loop that reduces the flow rate the valve-open time of valve 905 and decreases the dialysate (or substitution fluid) flow rate from dialysate line 918 and 919. As the monitored pressure reaches a desired threshold, valve 926 fully occludes and dialysate (or substitution fluid) flow rate ceases in lines 918 and 919.

After the red blood cell fluid mixture 914 exits the blood outlet of the plasma dialyzer, it passes through restriction valve 915 and then unites with cleansed blood 916. This mixture passes through venous drip chamber 933 and is returned to the patient (not shown).

Module bay 913 is indicated to illustrate that such a machine adaptation may be implemented through use of a machine module bay on existing hemodialysis machines such as the 2008T machine by the company Fresenius Medical Care. Implementation of such a module bay may require hydraulic changes, as is discussed in further detail elsewhere herein.

In this way, blood plasma generation is achieved concurrently with a hemodialysis therapy as blood plasma is separated from a portion of the whole blood that traverses through a first plasma dialyzer 906 with enhanced convective and diffusive mass transport of blood plasma constituents resultant of the use of dialysate or substitution fluid. A Red blood cell mixture is separated from the blood plasma constituents of the blood, and is returned to the patient concurrently with dialyzer blood exiting a third dialyzer 936. The blood plasma exiting the plasma dialyzer 906 undergoes plasmadiafiltration in a second dialyzer 920 and is recirculated as needed through pump 925, and is then collected in plasma collection bag 927.

Reference is now made to FIG. 10 which schematically illustrates a blood plasma and red blood cell generation device configured for generating blood plasma in accordance with the fourth embodiment of the system described herein. It should be appreciated that the system of FIG. 10 demonstrates only one embodiment of the system described herein, and that other possible configurations of the system described herein may be equally or even more suitable, depending on specific requirements. For example, an additional sterile filter may be used to generate substitution fluid instead of dialysate fluid.

The fresh dialysate fluid 1001 from the balancing system 1002 passes through a conductivity and temperature monitor (not shown), and then through a first sterile filter 1003 comprising a semipermeable membrane. Examples of such filters include the Diasafe Plus Filter by Fresenius Medical Care.

Cleansed dialysate fluid passes through line 1004. The cleansed dialysate fluid enters into four-way valve 1005 which accurately partitioned the cleansed dialysate fluid to a first dialysate line 1006, a second dialysate line 1007, and a third dialysate line 1022 through duty-cycling of the four-way valve 1005. It should be appreciated that a four-way valve is described; however, three individual valves may also be used if desired.

The first dialysate line 1006, the second dialysate line 1007, and the third dialysate line 1022 each have an associated pressure transducer (1008, 1009, and 1023 respectively) to assist with monitoring of pressure in dialysate lines 1006, 1007, and 1022. Cleansed dialysate fluid from the first line 1006 enters the dialysate inlet of the plasma dialyzer 1010.

The extracorporeal circuit, comprises a blood pump 1011, the blood portion of the plasma dialyzer 1010, and a plasma collection bag 1021. Additionally, the extracorporeal circuit includes a specialized intermediate blood plasma tubing line 1013, a second dialyzer 1018, a third dialyzer 1026, a modified arterial tube system 1012, a modified venous blood-tubing 1025 incorporating the venous drip chamber 1027, restriction valves 1015 and 1016 which ensure appropriate flow rates of the blood plasma fluid and red blood cell mixture exiting the plasma dialyzer, restriction valve 1024 that partitions a portion of the blood to the plasma dialyzer 1010, a recirculation valve 1019, a recirculation pump 1020, and an optional pressure sensor 1017.

A portion of the blood enters the blood inlet of the plasma dialyzer 1010. Plasma traverses the semipermeable membrane of the plasma dialyzer 1010 facilitated by the introduction of dialysate fluid into the plasma dialyzer 1010 via dialysate line 1006. Plasma exits into intermediate blood plasma tubing line 1013. Red blood cells exit the blood outlet of the plasma dialyzer 1010 via modified venous blood-tubing 1025. The red blood cell mixture passes a restriction valve 1015, unites with cleansed blood exiting a third dialyzer 1026. This mixture passes through venous drip chamber 1027, and then is returned to the patient (not shown).

Blood plasma constituents in the intermediate blood plasma tubing line 1013 pass through restriction valve 1016 and optional pressure sensor 1017, and then enter into a second dialyzer 1018. Cleansed blood plasma exits the blood outlet of the second dialyzer 1018, passes through a recirculation valve 1019, and then enters into a plasma collection bag 1021 with an air-permeable filter (not shown) to allow for air to vacate the plasma collection bag 1021. Recirculation pump 1020 remains off when cleansed blood plasma fluid enters into blood plasma collection bag 1021. When cleansed blood plasma is not being collected, recirculation pump 1020 turns on, restriction valve 1019 closes, and cleansed blood plasma is recirculated through the second dialyzer 1018. In this manner, blood plasma becomes further cleansed resulting in non-continuous delivery of multi-filtered, cleansed blood plasma in plasma collection bag 1021. Additionally, when cleansed blood is not being collected, restriction valve 1024 closes and fresh dialysate line 1006 is not supplied with dialysate through control of four-way valve 1005.

It should be appreciated, however, that fresh dialysate line 1006 may be supplied with a reduced amount of dialysate with concurrent duty-cycling of valve 1024 at a reduced rate to allow for continuous delivery of multi-filtered, cleansed blood plasma into collection bag 1021. In this case, valve 1019 and valve 1024 may periodically open to allow fluid to enter plasma collection bag 1021 at a rate equal to the flow rate of plasma exiting plasma dialyzer 1010 which may be based on the flow rate of whole blood through valve 1024.

Fresh dialysate from line 1007 passes through a pressure sensor 1009 and enters into the second dialyzer 1018. Duty-cycling of the fresh dialysate valves (valve 1005) allow the amount of fresh dialysate supplied to the first dialyzer 1010, the second dialyzer 1018, and the third dialyzer 1026 to be controlled. Concurrently, fresh dialysate from line 1022 passes through a pressure sensor 1023 and enters into the third dialyzer 1026. Spent dialysate fluid leaves the second dialyzer 1018 through spent dialysate line 1034, and then passes through a dialysate pressure monitor 1030, a three-way spent dialysate valve 1031, and a blood leak detector 1032. Concurrently, spent dialysate fluid leaves the third dialyzer 1026 through spent dialysate line 1028, and then passes through a dialysate pressure monitor 1029, a three-way valve 1030, and a blood leak detector 1032. This combined spent dialysate fluid then passes through the balancing system 1002 by means of a dialysate circulation pump 1033 and further to the drain (not shown). After passing through blood leak detector 1032, the spent dialysate enters an air separation chamber (not shown). Parallel to the balancing system 1002 there is a UF Pump 1014 to remove ultrafiltrate.

In this way, blood plasma generation is achieved concurrently with a hemodialysis therapy as a portion of the blood enters the first plasma dialyzer 1010, is separated from the red blood cell constituents of the blood facilitated by the diffusive and convective clearance achieved through use of dialysate or substitution fluid. Blood plasma enters a second dialyzer 1018, and is collected in a plasma collection bag 1021. The red blood cell constituents are returned to the patient concurrently as the other portion of the blood is dialyzed by a third dialyzer 1026 and returned to the patient.

Figure 11:
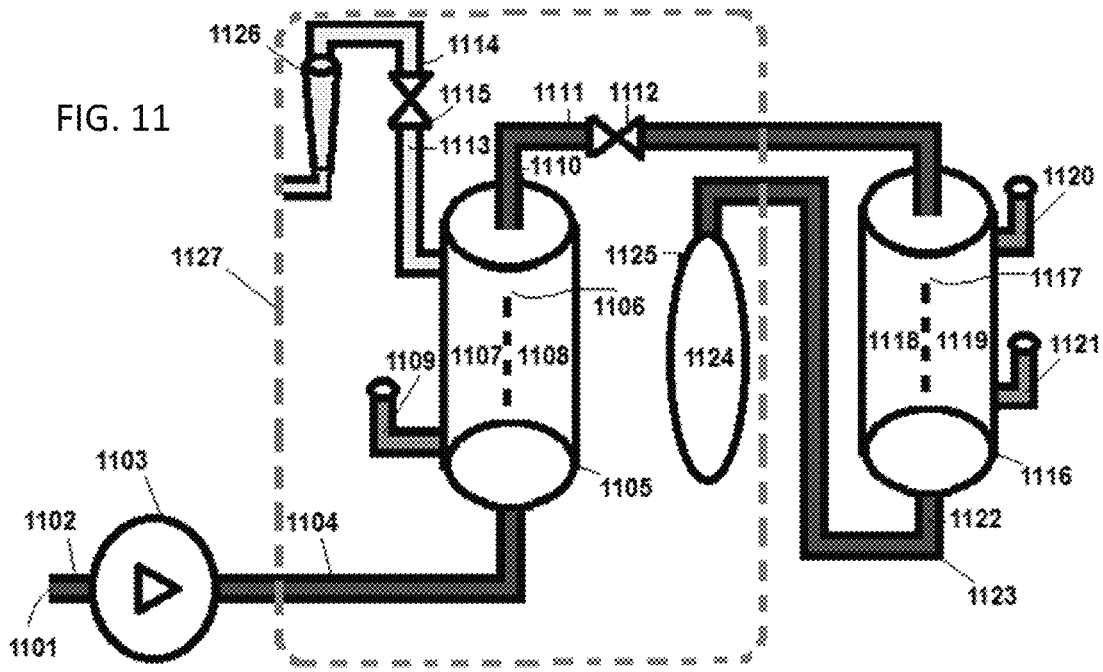
FIG. 11 is a schematic illustration of an extracorporeal blood circuit of a blood plasma and red blood cell generation device configured for collecting of red blood cells in accordance with the first embodiment of the system described herein.

Reference is now made to FIG. 11 which schematically illustrates a blood plasma and red blood cell generation device extracorporeal blood circuit configured for collecting red blood cells in accordance with the first embodiment of the system described herein. It should be appreciated that the system of FIG. 11 demonstrates only one embodiment of the system described herein, and that other possible configurations of the system described herein may be equally or even more suitable, depending on specific requirements.

In the system of FIG. 11 whole blood 1101 enters the pre-pump portion of the arterial blood line 1102 via blood pump 1103 and enters the post-pump portion of the arterial blood line 1104. The blood then enters a first plasma dialyzer 1105 after passing through blood flow and/or blood pressure monitoring devices (not shown) which send data to a control unit (not shown). The blood is carried by suitable tubing, for example, bloodline tubing made from flexible polyvinylchloride (PVC).

The first specialized dialyzer 1105 contains a semipermeable membrane 1106 that divides the dialyzer into a blood side component 1107 and a dialysate compartment 1108. As whole blood 1101 passes through blood compartment 1107, blood plasma, blood platelets, and other blood constituents (except the red blood cells) traverse the semipermeable membrane 1106 and enter the dialysate compartment 1108 of the plasma dialyzer. Fresh dialysate or substitution fluid is supplied to the first dialyzer from dialysate line 1109, and the blood plasma constituents (denoted 1113) exit the first plasma dialyzer 1105 via venous blood-tubing line 1114. The blood plasma traverses the semipermeable membrane 1106 by diffusion due to a difference in concentration of plasma constituents between blood compartment 1107 and dialysate compartment 1108 and by convection resultant of the addition of fresh dialysate or substitution fluid from dialysate line 1109. The dialyzer cartridge may be of any suitable type plasma dialyzer. For example, such filters may include the Evacure and Evaclio plasma separators from LINC medical, the Monet filter from Fresenius Medical Care, and the PlasmaFlo™ from Apheresis Technologies, Inc.

The blood plasma constituents 1113 exiting the plasma dialyzer 1105 enters venous blood-tubing line 1114 and passes through a restriction valve 1115. At the same time, the red blood cells incapable of traversing the semipermeable membrane 1106, along with dialysate or substitution fluid and other whole blood constituents (denoted 1110) exit the blood outlet of the plasma dialyzer 1105 via intermediate blood-tubing 1111 and passes through a restriction valve 1112. The restriction valve 1112 on intermediate blood-tubing 1111 ensures that the flow rate at the blood outlet of the plasma dialyzer 1105 is controlled and is less than the flow rate of whole blood 1101 entering the blood inlet of the plasma dialyzer 1105. Restriction valve 1115 ensures that the flow rate of blood plasma constituents 1113 in venous blood-tubing line 1114 does not exceed a desired rate. Additionally, the concurrent restriction action of restriction valve 1112 guarantees a minimum flow rate of blood plasma constituents 1113 in venous blood-tubing line 1114.

After the red blood cell mixture 1110 exit restriction valve 1112, this mixture enters a second standard dialyzer 1116 containing a semi permeable membrane 1117 which divides the second dialyzer 1116 into a blood compartment 1118 and a dialysate compartment 1119.

As the red blood cell mixture 110 passes through blood compartment 1118, some of the smaller red blood cell mixture constituents traverse the semipermeable membrane 1117. These red blood cell mixture constituents, such as uremic toxins, travel across semipermeable membrane 1117 by diffusion due to concentration gradient between the blood plasma in blood compartment 1118 and dialysate in dialysate compartment 1119. Fresh dialysate is supplied to the second dialyzer from dialysate line 1120, and spent dialysate is removed from the second dialyzer 1116 by dialysate line 1121. Alternatively, fresh dialysate may be supplied by dialysate line 1121 and spent dialysate may be removed from the second dialyzer 1116 by dialysate line 1120 to allow for dialysate to run counter-parallel to the red blood cell mixture flow direction. The dialyzed red blood cell mixture 1122 exits the second dialyzer 1116, enters tubing line 1123 and then enters a red blood cell collection bag 1124 with associated blood pressure monitoring devices (not shown) which send this pressure data to a control unit (not shown). An air-permeable filter 1125 allows for air, but not fluid, to vacate red blood cell collection bag 1124. Increases in pressure resultant from the red blood cell collection bag 1124 beginning to expand may be detected by the associated blood pressure monitoring devices and result in initiation of a negative feedback loop that reduces the flow rate of whole blood 1101 and dialysate (or substitution fluid) from dialysate line 1109. As the monitored pressure reaches a desired threshold, restriction valve 1112 fully occludes, and the remaining blood constituents are returned to the patient (not shown) through the venous drip chamber 1126 of venous tubing 1114 and associated blood pressure monitoring devices (not shown) which send this pressure data to a control unit (not shown).

Module bay 1127 is indicated to illustrate that such a machine adaptation may be implemented through use of a machine module bay on existing hemodialysis machines such as the 2008T machine by the company Fresenius Medical Care. Implementation of such a module bay may require hydraulic changes, as is discussed in further detail elsewhere herein.

In this way, red blood cell collection is achieved with use of dialysate (or substitution fluid) as blood enters the first plasma dialyzer 1105, is separated from the red blood cell constituents of the blood facilitated by the diffusive and convective clearance achieved through use of dialysate fluid. The blood plasma constituents are returned to the patient, while the red blood cell mixture concurrently enters a second dialyzer 1116 to be cleansed and is then collected in a red blood cell collection bag 1124.

Figure 12:
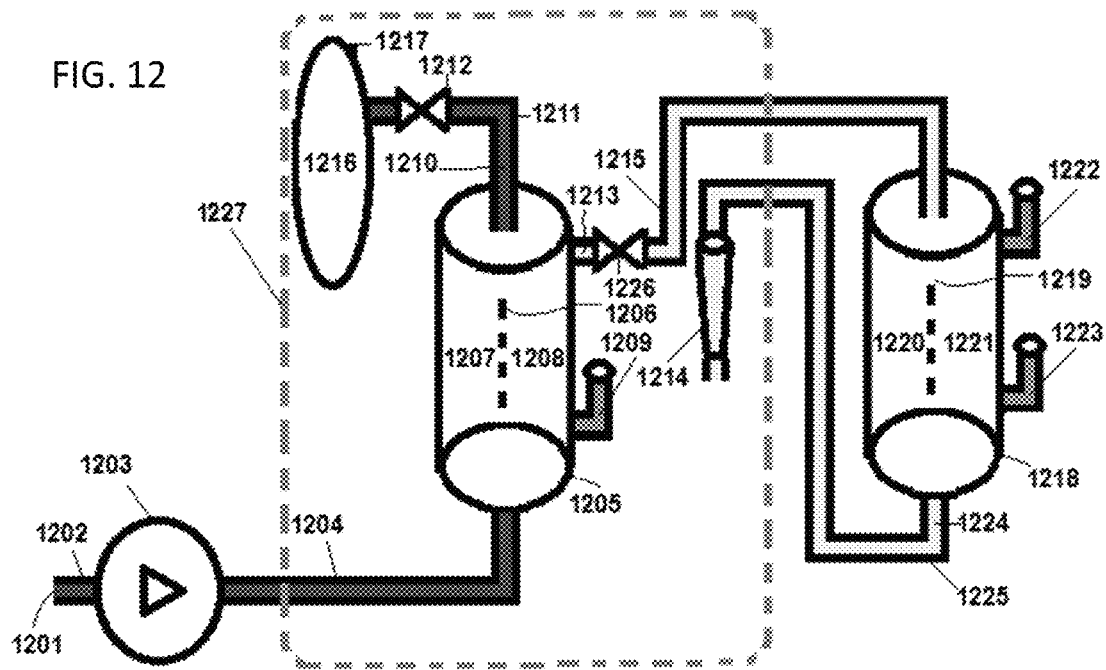
FIG. 12 is a schematic illustration of an extracorporeal blood circuit of a blood plasma and red blood cell generation device configured for the collecting of red blood cells in accordance with the second embodiment of the system described herein.

Reference is now made to FIG. 12 which schematically illustrates a blood plasma and red blood cell generation device extracorporeal blood circuit configured for collecting red blood cells in accordance with the second embodiment of the system described herein. It should be appreciated that the system of FIG. 12 demonstrates only one embodiment of the system described herein, and that other possible configurations of the system described herein may be equally or even more suitable, depending on specific requirements. For example, the physical lengths and diameters of blood-tubing comprising the extracorporeal may be interchanged or adjusted, as long as the underlying functionality of the extracorporeal blood circuit remains unchanged.

In the system of FIG. 12 whole blood 1201 enters the pre-pump portion of the arterial blood line 1202 via blood pump 1203 and enters the post-pump portion of the arterial blood line 1204. The blood then enters a first plasma dialyzer 1205 after passing through blood flow and/or blood pressure monitoring devices (not shown) which send data to a control unit (not shown). The blood is carried by suitable tubing, for example, bloodline tubing made from flexible polyvinyl-chloride (PVC).

The first specialized dialyzer 1205 contains a semipermeable membrane 1206 that divides the dialyzer into a blood side component 1207 and a dialysate compartment 1208. As whole blood 1201 passes through blood compartment 1207, blood plasma, blood platelets, and other blood constituents (except the red blood cells) traverse the semipermeable membrane 1206 and enter the dialysate compartment 1208 of the plasma dialyzer. Fresh dialysate (or substitution fluid) is supplied to the first dialyzer from dialysate line 1209, and the blood plasma constituents (denoted 1213) exit the first plasma dialyzer 1205 via intermediate blood-tubing line 1215. The blood plasma traverses the semipermeable membrane 1206 by diffusion due to a difference in concentration of plasma constituents between blood compartment 1207 and dialysate compartment 1208 and by convection resultant of the addition of fresh dialysate or substitution fluid from dialysate line 1209. The dialyzer cartridge may be of any suitable type plasma dialyzer. For example, such filters include the Evacure and Evaclio plasma separators from LINC medical, the Monet filter from Fresenius Medical Care, and the PlasmaFlo™ from Apheresis Technologies, Inc.

The red blood cells (denoted 1210) incapable of traversing the semipermeable membrane 1206 exiting the plasma dialyzer 1205 enters blood-tubing line 1211 and passes through a restriction valve 1212. At the same time, the blood plasma constituents 1213 exit the plasma dialyzer 1205 via intermediate blood-tubing line 1215. The restriction valve 1212 on blood-tubing line 1211 ensures that the flow rate at the blood outlet of the plasma dialyzer 1205 is controlled and is less than the flow rate of whole blood 1201 entering the blood inlet of the plasma dialyzer 205. Restriction valve 1226 ensures that the flow rate of blood plasma constituents 1213 in blood plasma tubing line 1215 does not exceed a desired rate. Additionally, the concurrent restriction action of restriction valve 1212 guarantees a minimum flow rate of blood plasma constituents 1213 in blood plasma tubing line 1215.

After the red blood cell mixture 1210 exit restriction valve 1212, this mixture enters a red blood cell collection bag 1216 with associated blood pressure monitoring devices (not shown) which send this pressure data to a control unit (not shown). An air-permeable filter 217 allows for air, but not fluid, to vacate red blood collection bag 1216. Increases in pressure resultant from the red blood cell collection bag 1216 beginning to expand may be detected by the associated blood pressure monitoring devices and result in initiation of a negative feedback loop that reduces the flow rate of whole blood 1201 and dialysate (or substitution fluid) from dialysate line 1209.

After blood plasma constituents 1213 travels through restriction valve 1226 the blood plasma constituents enter a second dialyzer 1218 containing a semi permeable membrane 1219 which divides the second dialyzer 1218 into a blood compartment 1220 and a dialysate compartment 1221.

As the blood plasma constituents 1213 passes through blood compartment 220, plasmadiafiltration occurs resulting in some of the smaller remaining plasma constituents, such as uremic toxins, traversing the semipermeable membrane 1219. These constituents travel across semipermeable membrane 1219 by diffusion due to concentration gradient between the blood plasma constituents 1213 in blood compartment 1220 and dialysate (or substitution fluid) in dialysate compartment 1221. Fresh dialysate (or substitution fluid) is supplied to the second dialyzer from dialysate line 1222, and spent dialysate is removed from the second dialyzer 1218 by dialysate line 1223. Alternatively, fresh dialysate may be supplied by dialysate line 1223 and spent dialysate may be removed from the second dialyzer 1218 by dialysate line 1222 to allow for dialysate to run counter-parallel to the blood plasma flow direction. The dialyzed blood plasma 1224 exits the second dialyzer 1218, and enters venous blood-tubing line 1225 and then enters a venous drip chamber 1226 with associated blood pressure monitoring devices (not shown) which send this pressure data to a control unit (not shown) and is returned to the patient (not shown).

As the monitored pressure reaches a desired threshold in red blood cell collection bag 1216, restriction valve 1212 fully occludes, and the remaining blood constituents are returned to the patient (not shown) through the venous blood chamber 1226 of venous tubing 1225 and associated blood pressure monitoring devices (not shown) which send this pressure data to a control unit (not shown).

Module bay 1227 is indicated to illustrate that such a machine adaptation may be implemented through use of a machine module bay on existing hemodialysis machines such as the 2008T machine by the company Fresenius Medical Care. Implementation of such a module bay may require hydraulic changes, as is discussed in further detail elsewhere herein.

In this way, red blood cell collection is achieved with use of dialysate (or substitution fluid) as blood enters the first plasma dialyzer 1205, is separated from the red blood cell constituents of the blood facilitated by the diffusive and convective clearance achieved through use of dialysate fluid. The blood plasma constituents 1213 enters a second dialyzer 1218 and is then returned to the patient, while red blood cells are concurrently collected in a red blood cell collection bag 1216.

Figure 13:
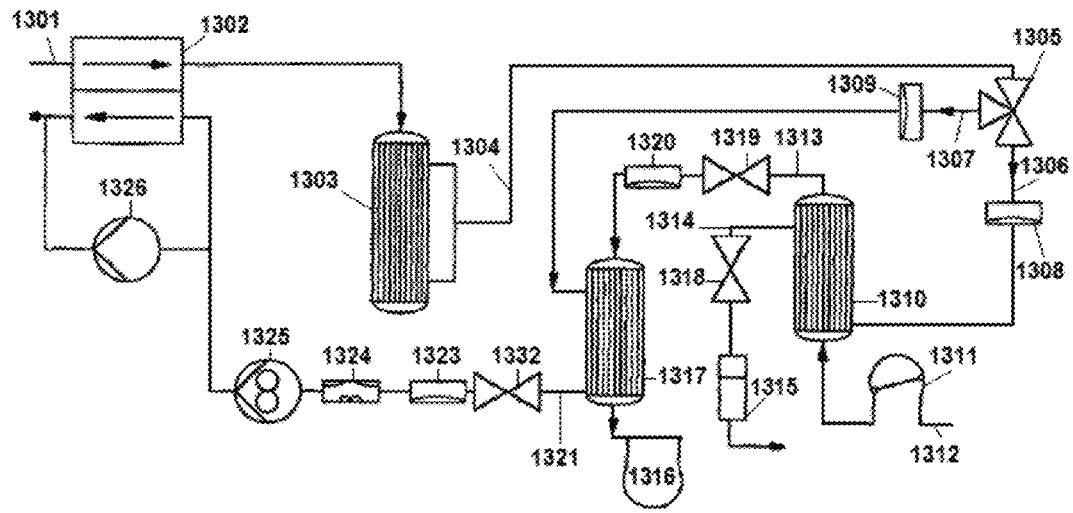
FIG. 13 is a schematic illustration of a blood plasma and red blood cell generation device configured for collecting red blood cells in accordance with the first embodiment of the system described herein.

Reference is now made to FIG. 13 which schematically illustrates a blood plasma and red blood cell generation device configured for collecting red blood cells in accordance with the first embodiment of the system described herein.

The fresh dialysate fluid 1301 from the balancing system 1302 passes through a conductivity and temperature monitor (not shown) which prevent incorrect dialysate fluid composition and/or temperature from reaching the patient, and then through a first sterile filter 1303 comprising a semipermeable membrane. Examples of such filters include the Diasafe Plus Filter by Fresenius Medical Care.

The dialysis fluid passes through the membrane of the sterile filter 1303 to a line 1304 for producing a cleansed dialysate fluid. The cleansed dialysate fluid enters into three-way valve 1305. Three-way valve 1305 proportions the cleansed dialysate fluid, through use of software-duty cycling. Through use of duty-cycling of valves, or in other words toggling the valves off and on at known rates, a total amount of cleansed dialysate fluid can be accurately partitioned to a first dialysate line 1306, and a second dialysate line 1307. It should be appreciated that a three-way valve is described; however, two individual valves may also be used if desired.

A fraction of the dialysate fluid travels through both line 1306 and 1307 concurrently. The first dialysate line 1306 and second dialysate line 1307 each have an associated pressure transducer 1308 and 1309 to assist with monitoring of pressure in dialysate lines 1306 and 1307. Cleansed dialysate fluid from the first line 1306 enters the dialysate inlet of the plasma dialyzer 1310.

The extracorporeal circuit comprises a blood pump 1311, an arterial tube system 1312, the blood portion of the plasma dialyzer 1310, an intermediate blood plasma tubing line 1313, a venous blood-tubing 1314 incorporating the venous drip chamber 1315, and a red blood cell collection bag 1316. Additionally, the extracorporeal circuit comprises a second dialyzer 1317, restriction valves 1318 and 1319 which ensure appropriate flow rates of the blood plasma fluid and red blood cell mixture exiting the plasma dialyzer 1310, and an optional pressure sensor 1320.

Blood enters the blood inlet of the plasma dialyzer 1310. Plasma traverses the semipermeable membrane of the plasma dialyzer 1310 facilitated by the introduction of cleansed dialysate fluid into the plasma dialyzer 1310 via dialysate line 1306. Red blood cells incapable of traversing the semipermeable membrane along with dialysate fluid and other whole blood constituents exit the blood outlet of the plasma dialyzer 1310 via intermediate blood-tubing 1313. The red blood cell mixture passes a restriction valve 1319 which ensures the flow rate of the red blood cell mixture does not exceed the flow rate of whole blood into the plasma dialyzer 1310. The red blood cell mixture then travels through an optional pressure sensor 1320. Optional pressure sensor 1320 allows for pressure monitoring in intermediate blood-tubing 1313. After traversing the intermediate blood plasma tubing 1313, the blood plasma constituents enters into a second dialyzer 1317.

The red blood cell mixture enters the blood inlet of a second dialyzer 1317, and cleansed a cleansed red blood cell mixture exits the blood outlet of the second dialyzer 1317 and enters into a red blood cell collection bag 1316 with an air-permeable filter (not shown) to allow for air to vacate the red blood cell collection bag as cleansed blood plasma enters the plasma collection bag 1316.

Fresh dialysate from line 1307 passes through a pressure sensor 1309 and enters into the second dialyzer 1317. Duty-cycling of the fresh dialysate valves (valve 1305) allow the amount of fresh dialysate supplied to the first dialyzer 1310 and second dialyzer 1317 to be controlled. Fresh dialysate facilitates diffusion of smaller constituents of the red blood cell mixture, such as uremic toxins, into the dialysate compartment of the second dialyzer 1317. Spent dialysate fluid leaves the second dialyzer 1317 through a spent dialysate line 1321, and passes through a spent dialysate valve 1322, a dialysate pressure monitor 1323, and a blood leak detector 1324. The spent dialysate passes through the balancing system 1302 by means of a dialysate circulation pump 1325 and further to the drain (not shown). After passing through blood leak detector 1324, the spent dialysate enters an air separation chamber (not shown), which makes possible the separation of air, since many balancing systems are disturbed by air. Parallel to the balancing system 1302 there is a UF Pump 1326 to remove ultrafiltrate.

Concurrently, separated blood plasma constituents exit the dialysate port outlet of the plasma dialyzer 1310 into a venous blood line 1314. The blood plasma constituents then pass a restriction valve 1318, enter a venous drip chamber 315, and then are returned to the patient (not shown). Restriction valve 1318 ensures the flow rate of the blood plasma constituents does not exceed a desired threshold. Additionally, the restriction valves 1319 together with restriction valve 1318 ensure minimum flow rates at the blood outlet and dialysate outlet of the plasma dialyzer 1310.

In this way, red blood cell collection is achieved as blood plasma is separated from whole blood through traversal through the first plasma dialyzer 1310 with enhanced convective and diffusive mass transport of blood plasma constituents resultant of the use of dialysate fluid. The red blood cell mixture is separated from the blood plasma constituents of the blood, enters into a second dialyzer 1317, and is collected in a red blood cell collection bag 1316. The blood plasma constituents along with dialysate (or substitution fluid) are returned to the patient with real-time monitoring of venous pressure and level detector monitoring for detecting air.

Figure 14:
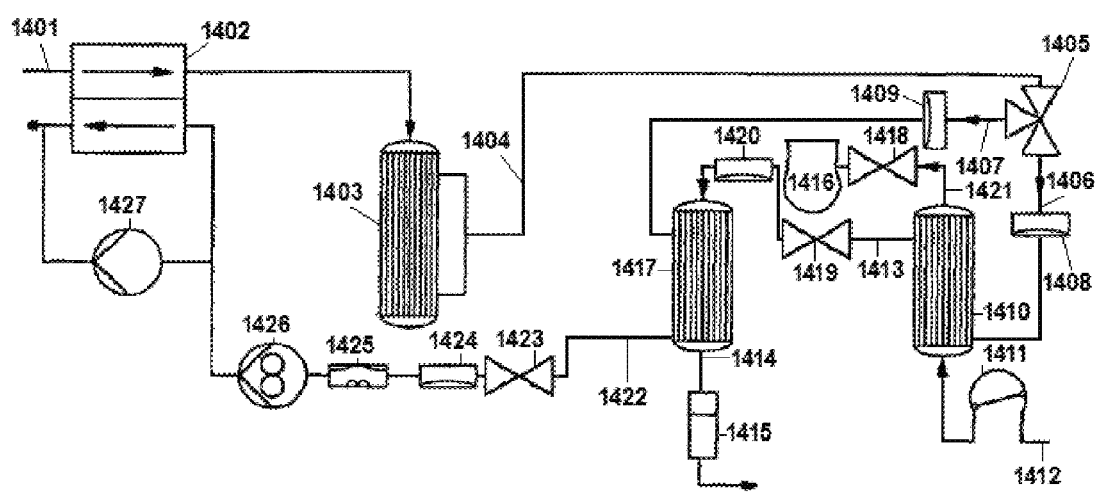
FIG. 14 is schematic illustration of a blood plasma and red blood cell generation device configured for collecting red blood cells in accordance with the second embodiment of the system described herein.

Reference is now made to FIG. 14 which schematically illustrates a blood plasma and red blood cell generation device configured collecting red blood cells in accordance with the second embodiment of the system described herein.

The fresh dialysate fluid 1401 from the balancing system 1402 passes through a conductivity and temperature monitor (not shown), and then through a first sterile filter 1403 comprising a semipermeable membrane. Examples of such filters include the Diasafe Plus Filter by Fresenius Medical Care.

Cleansed dialysate fluid passes through line 1404. The cleansed dialysate fluid enters into three-way valve 1405 which accurately partitioned the cleansed dialysate fluid to a first dialysate line 1406 and toward a second dialysate line 1407 through duty-cycling of three-way valve 1405. The first dialysate line 1406 and second dialysate line 1407 each have an associated pressure transducer 1408 and 1409 to assist with monitoring of pressure in dialysate lines 1406 and 1407. Cleansed dialysate fluid from the first line 1406 enters the dialysate inlet of the plasma dialyzer 1410.

The extracorporeal circuit comprises a blood pump 1411, an arterial tube system 1412, the blood portion of the plasma dialyzer 1410, an intermediate blood plasma tubing line 1413, a venous blood-tubing 1414 incorporating the venous drip chamber 1415, and a red blood cell collection bag 1416. Additionally, the extracorporeal circuit comprises a second dialyzer 1417, restriction valves 1418 and 1419 which ensure appropriate flow rates of the blood plasma fluid and red blood cell mixture exiting the plasma dialyzer 1410, intermediate red blood cell line 1421 and an optional pressure sensor 1420.

Blood enters the blood inlet of the plasma dialyzer 1410. Plasma traverses the semipermeable membrane of the plasma dialyzer 1410 facilitated by the introduction of cleansed dialysate fluid into the plasma dialyzer 1410 via dialysate line 1406. Red blood cells incapable of traversing the semipermeable membrane along with dialysate fluid and other whole blood constituents exit the blood outlet of the plasma dialyzer 1410 into the intermediate red blood cell line 1421. The red blood cell mixture passes a restriction valve 1418 which ensures the flow rate of the red blood cell mixture does not exceed the flow rate of whole blood into the plasma dialyzer 1410. After traversing the intermediate red blood cell line 1421, the red blood cell mixture enters into a red blood cell collection bag 1416 with an air-permeable filter (not shown) to allow for air to vacate the red blood cell collection bag as red blood cells enter the red blood cell collection bag 1416.

Separated blood plasma constituents exit the dialysate port outlet of the plasma dialyzer 1410 through intermediate blood plasma tubing line 1413, and passes through restriction valve 1419 which ensures the flow rate of the blood plasma constituents does not exceed a desired threshold. Additionally, the restriction valves 1419 together with restriction valve 1418 ensure minimum flow rates at the blood outlet and dialysate outlet of the plasma dialyzer 1410.

After passing restriction valve 1419, the blood plasma constituents passes an optional pressure sensor 1420 and then enters the blood inlet of a second dialyzer 1417. Cleansed blood plasma exits the blood outlet of the second dialyzer 1417, enters a venous drip chamber 1415, and then is returned to the patient (not shown).

Fresh dialysate from line 1407 passes through a pressure sensor 1409 and enters into the second dialyzer 1417. Duty-cycling of the fresh dialysate valves (valve 1405) allow the amount of fresh dialysate supplied to the first dialyzer 1410 and second dialyzer 1417 to be controlled. Fresh dialysate facilitates diffusion of smaller blood plasma constituents, such as uremic toxins, into the dialysate compartment of the second dialyzer 1417. Spent dialysate fluid leaves the second dialyzer 1417 through a spent dialysate line 1422, and passes through a spent dialysate valve 1423, a dialysate pressure monitor 1424, and a blood leak detector 1425. The spent dialysate passes through the balancing system 1402 by means of a dialysate circulation pump 1426 and further to the drain (not shown). After passing through blood leak detector 1425, the spent dialysate enters an air separation chamber (not shown), which makes possible the separation of air, since many balancing systems are disturbed by air. Parallel to the balancing system 1402 there is a UF pump 1427 to remove ultrafiltrate.

In this way, red blood cell collection is achieved as blood plasma is separated from whole blood through traversal through the first plasma dialyzer 1410 with enhanced convective and diffusive mass transport of blood plasma constituents resultant of the use of dialysate fluid. The blood plasma constituents are separated from the red blood cell components of the blood, enters into a second dialyzer 1417, and is returned to the patient. The red blood cell mixture is collected in red blood cell collection bag 1416.

Figure 15:
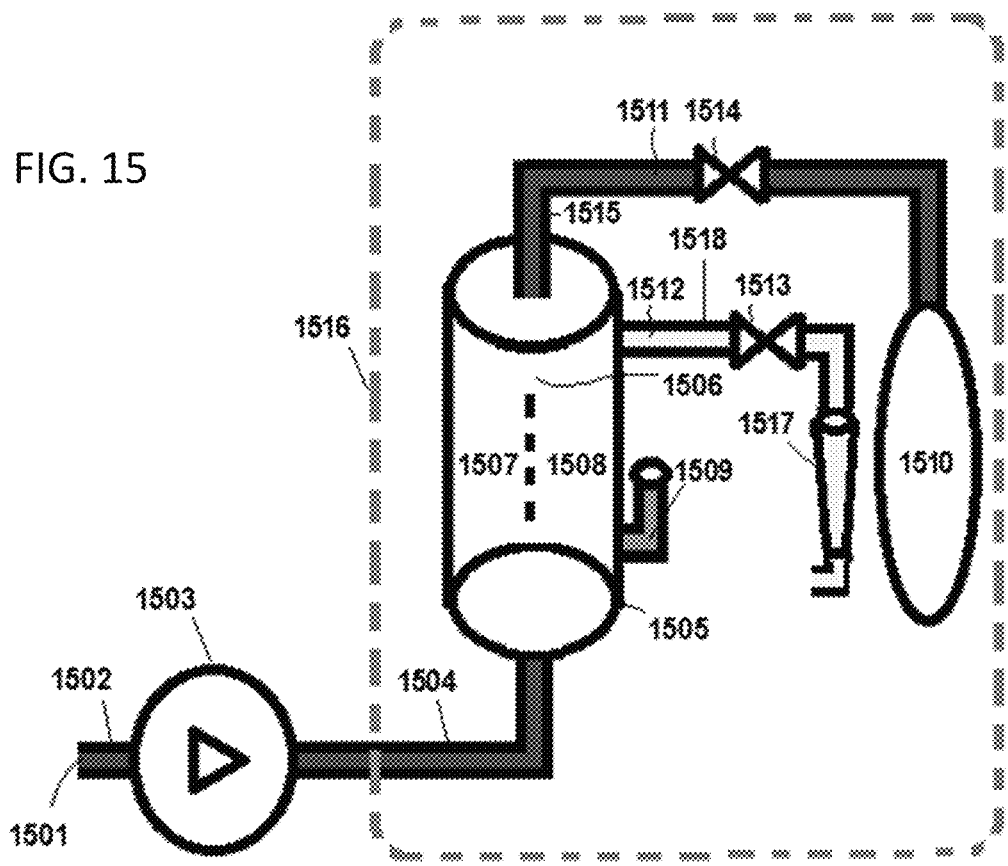
FIG. 15 is a schematic illustration of an extracorporeal blood circuit of a blood plasma and red blood cell generation device configured for collecting red blood cells in accordance with the third embodiment of the system described herein.

Reference is now made to FIG. 15 which schematically illustrates a blood plasma and red blood cell generation device extracorporeal blood circuit configured for collecting red blood cells in accordance with the third embodiment of the system described herein. It should be appreciated that the system of FIG. 15 demonstrates only one embodiment of the system described herein, and that other possible configurations of the system described herein may be equally or even more suitable, depending on specific requirements. For example, the physical lengths and diameters of blood-tubing comprising the extracorporeal may be interchanged or adjusted, as long as the underlying functionality of the extracorporeal blood circuit remains unchanged.

In the system of FIG. 15 whole blood 1501 enters the pre-pump portion of the arterial blood line 1502 via blood pump 1503 and enters the post-pump portion of the arterial blood line 1504. The blood then enters a first plasma dialyzer 1505 after passing through blood flow and/or blood pressure monitoring devices (not shown) which send data to a control unit (not shown). The blood is carried by suitable tubing, for example, bloodline tubing made from flexible polyvinyl-chloride (PVC).

The specialized dialyzer 1505 contains a semipermeable membrane 1506 that divides the dialyzer into a blood side component 1507 and a dialysate compartment 1508. As whole blood 1501 passes through blood compartment 1507, blood plasma, blood platelets, and other blood constituents (except the red blood cells) traverse the semipermeable membrane 1506 and enter the dialysate compartment 1508 of the plasma dialyzer. Fresh dialysate or substitution fluid is supplied to the dialyzer from dialysate line 1509, and the blood plasma constituents (denoted 1512) exit the first plasma dialyzer 1505 via venous blood-tubing line 1518. The blood plasma traverses the semipermeable membrane 1506 by diffusion due to a difference in concentration of plasma constituents between blood compartment 1507 and dialysate compartment 1508 and by convection resultant of the addition of fresh dialysate or substitution fluid from dialysate line 1509. The dialyzer cartridge may be of any suitable type plasma dialyzer. For example, such filters include the Evacure and Evaclio plasma separators from LINC medical, the Monet filter from Fresenius Medical Care, and the PlasmaFlo™ from Apheresis Technologies, Inc.

The blood plasma constituents 1512 exiting the plasma dialyzer 1505 enters venous blood-tubing line 1518 and passes through a restriction valve 1513. At the same time, the red blood cells incapable of traversing the semipermeable membrane 1506, along with dialysate or substitution fluid and other whole blood constituents (denoted 1511) exit the blood outlet of the plasma dialyzer 1505 via intermediate blood-tubing line 1515. The restriction valve 1514 on blood-tubing line 1515 ensures that the flow rate at the blood outlet of the plasma dialyzer 1505 is controlled and is less than the flow rate of whole blood 1501 entering the blood inlet of the plasma dialyzer 1505. Restriction valve 1513 ensures that the flow rate of blood plasma constituents 1512 in venous blood-tubing line 1518 does not exceed a desired rate. Additionally, the concurrent restriction action of restriction valve 1514 guarantees a minimum flow rate of blood plasma constituents 1512 in venous blood-tubing line 1518.

After the red blood cell mixture 1511 exit restriction valve 1514, this mixture enters a red blood cell collection bag chamber 1510 with associated blood pressure monitoring devices (not shown) which send this pressure data to a control unit (not shown). An air-permeable filter (not shown) allows for air, but not fluid, to vacate the red blood cell collection bag 1510. Increases in pressure resultant from the red blood cell collection bag 1510 beginning to expand may be detected by the associated blood pressure monitoring devices and result in initiation of a negative feedback loop that reduces the flow rate of whole blood 1501 and dialysate (or substitution fluid) from dialysate line 1509.

After the blood plasma constituents 1512 exits the plasma dialyzer, it then travels through restriction valve 1513 and enters venous blood-tubing line 1518 and then enters a venous drip chamber 1517 with associated blood pressure monitoring devices (not shown) which send this pressure data to a control unit (not shown) and is returned to the patient (not shown).

As the monitored pressure reaches a desired threshold in the red blood cell collection bag 1510, restriction valve 1514 fully occludes, and the remaining blood constituents are returned to the patient (not shown) through the venous blood chamber 1517 of venous tubing 1518 and associated blood pressure monitoring devices (not shown) which send this pressure data to a control unit (not shown).

Module bay 1516 is indicated to illustrate that such a machine adaptation may be implemented through use of a machine module bay on existing hemodialysis machines. Implementation of such a module bay may require hydraulic changes, as is discussed in further detail elsewhere herein.

In this way, red blood cell collection is achieved as blood plasma is separated from whole blood through traversal through the first plasma dialyzer 1505 with enhanced convective and diffusive mass transport of blood plasma constituents resultant of the use of dialysate or substitution fluid. The blood plasma constituents are separated from the red blood cells components of the blood, and is returned to the patient. The red blood cell mixture is collected in red blood cell collection bag 1510.

Figure 16:
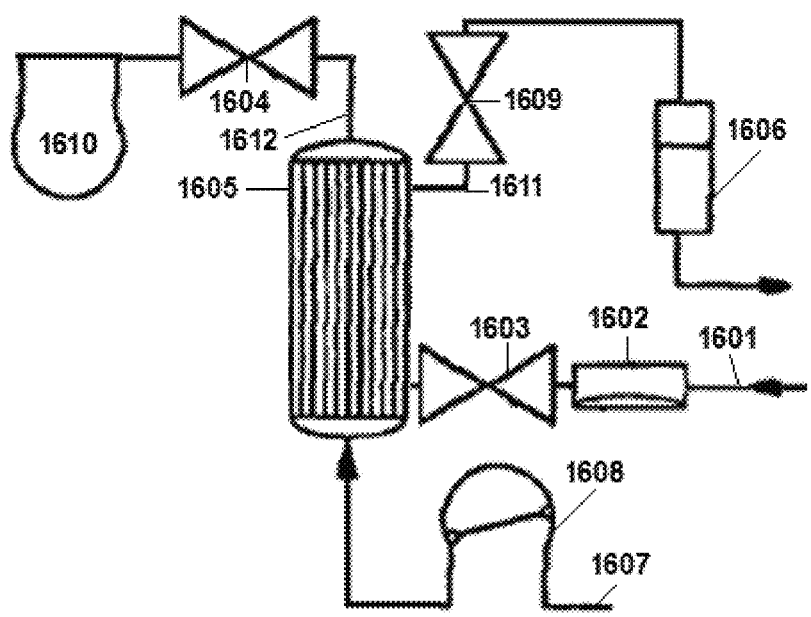
FIG. 16 is schematic illustration of a blood plasma and red blood cell generation device configured for collecting red blood cells in accordance with the third embodiment of the system described herein.

Reference is now made to FIG. 16 which schematically illustrates a blood plasma and red blood cell generation device configured for collecting red blood cells in accordance with the third embodiment of the system described herein. The dialysate solution used for the system described herein may be prepared as follows. A suitable quality of water, such as reverse osmosis water, is provided from a water source (not shown). The water enters a water preparation module (not shown) that heats and degasses the water. Any suitable heating and degassing module may be used in conjunction with the system described herein. The degassed, heated water is proportioned with acid and bicarbonate to generate fresh dialysate fluid. The fresh dialysate fluid 1601 passes through a conductivity and temperature monitor (not shown) which prevent incorrect dialysate fluid composition and/or temperature from reaching the patient, and then through a first sterile filter (not shown) comprising a semipermeable membrane producing cleansed dialysate and then optionally through a second sterile filter (not shown) comprising a semipermeable membrane producing substitution fluid. The cleansed dialysate or substitution fluid then passes through an associated pressure transducer 1602 and then passes through bypass valve 1603. After passing through bypass valve 1603, the cleansed dialysate or substitution fluid enters the dialysate inlet of the plasma dialyzer 1605.

The extracorporeal circuit comprises a blood pump 1608, an arterial tube system 1607, the blood portion of the plasma dialyzer 1605, an intermediate blood-tubing line 1612, a venous blood-tubing 1611 incorporating the venous drip chamber 1606, and a red blood cell collection bag 1610. Additionally, the extracorporeal circuit comprises restriction valves 1609 and 1604 which ensure appropriate flow rates of the blood plasma fluid and red blood cell mixture exiting the plasma dialyzer 1605.

Blood enters the blood inlet of the plasma dialyzer 1605 and traverses the semipermeable membrane facilitated by the introduction of cleansed dialysate fluid or substitution fluid. Red blood cells incapable of traversing the semipermeable membrane along with dialysate fluid and other whole blood constituents exit the blood outlet of the plasma dialyzer 1605 via intermediate blood-tubing line 1612. The red blood cell mixture passes a restriction valve 1604, and enters into a red blood cell collection bag 1610 with an air-permeable filter (not shown) to allow for air to vacate the red blood cell collection bag as the red blood cell mixture enters the red blood cell collection bag 1610. Restriction valve 1604 ensures that the flow rate of whole blood into the plasma dialyzer 1605 is greater than the flow rate of the red blood cell mixture exiting the blood outlet of the plasma dialyzer 1605.

Separated blood plasma constituents exit the dialysate port outlet of the plasma dialyzer 1605 through venous blood-tubing line 1611, and passes through restriction valve 1609 which ensures the flow rate of the blood plasma constituents does not exceed a desired threshold. Additionally, the restriction valves 1609 together with restriction valve 1604 ensure minimum flow rates at the blood outlet and dialysate outlet of the plasma dialyzer 1605. After passing restriction valve 1609, the blood plasma enters a venous drip chamber 1606, and then is returned to the patient (not shown).

In this way, red blood cell generation is achieved as blood plasma is separated from whole blood through traversal through the first plasma dialyzer 1605 with enhanced convective and diffusive mass transport of blood plasma constituents resultant of the use of dialysate or substitution fluid. Red blood cells are separated from the blood plasma constituents of the blood and are collected in red blood cell collection bag 1610. The blood plasma constituents along with dialysate (or substitution fluid) are returned to the patient with real-time monitoring of venous pressure and level detector monitoring for detecting air.

Various embodiments discussed herein may be combined with each other in appropriate combinations in connection with the system described herein. Additionally, in some instances, the order of steps in described flow processing may be modified, where appropriate. Further, various aspects of the system described herein may be implemented or controlled using software, hardware, a combination of software and hardware and/or other computer-implemented or computer-controlled modules or devices having described features and performing described functions. The system may further include a display and/or other computer components for providing a suitable interface with a user and/or with other computers.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A blood processing device, comprising:
an extracorporeal circuit having:
at least a first dialyzer and a second dialyzer, wherein the first dialyzer has fibers with a first pore size, and wherein the second dialyzer is located downstream of a dialysate outlet port of the first dialyzer and has fibers with a second pore size that is smaller than the first pore size;
a first restriction valve located downstream of the dialysate outlet port of the first dialyzer and upstream of the second dialyzer; and
a second restriction valve located downstream of a blood outlet port of the first dialyzer,
wherein the first restriction valve and the second restriction valve are configured to maintain a flow rate of plasma and dialysate from the dialysate outlet port of the first dialyzer below a threshold, wherein the second restriction valve is configured to control a flow rate of blood at the blood outlet port of the first dialyzer to be less than a flow rate of whole blood entering a blood inlet port of the first dialyzer, and wherein restriction action of the second restriction valve is controlled to ensure at least a minimum flow rate of plasma and dialysate is maintained from the dialysate outlet port of the first dialyzer.

2. The blood processing device according to claim 1, wherein the second dialyzer is a standard dialyzer having fibers with a pore size characterized by a molecular weight cut off around 60,000 daltons, and wherein the first dialyzer is a plasma dialyzer having fibers with a pore size characterized by a molecular weight cut off greater than 60,000 daltons.

3. The blood processing device according to claim 1, further comprising:
a control unit that controls fluid flow rates among components of the extracorporeal circuit.

4. The blood processing device according to claim 3, wherein the control unit further controls modality of the device to collect blood plasma and/or red-blood cells.

5. The blood processing device according to claim 1, wherein the first dialyzer and the second dialyzer each include a semipermeable membrane, and wherein blood plasma produced by the first dialyzer is directed to an inlet port of the second dialyzer located downstream of the first dialyzer.

6. The blood processing device according to claim 1, further comprising:
a plasma bag, wherein plasma exiting the second dialyzer may enter into the plasma bag for collection.

7. The blood processing device according to claim 1, further comprising:
a recirculation loop that connects the extracorporeal circuit directly after the second dialyzer to the extracorporeal circuit directly before the second dialyzer.

8. The blood processing device according to claim 7, wherein blood plasma in the recirculation loop is repeatedly cycled through the second dialyzer.

9. The blood processing device according to claim 1, further comprising:
a third dialyzer arranged in parallel with the first dialyzer and/or the second dialyzer.

10. The blood processing device according to claim 9, wherein the third dialyzer is a standard dialyzer that allows for concurrent hemodialysis, while the first dialyzer and the second dialyzer allow for plasma filtration and/or plasma-diafiltration.

11. The blood processing device according to claim 1, further comprising:
an adsorbent cartridge disposed downstream of the first dialyzer.

12. The blood processing device according to claim 11, wherein the adsorbent cartridge is disposed upstream of the second dialyzer to reduce the concentrate of specific plasma constituents before entering the second dialyzer.

13. The blood processing device according to claim 11, wherein the adsorbent cartridge is disposed downstream of the second dialyzer such that the flow rate of the blood plasma in the extracorporeal circuit between the first dialyzer and second dialyzer is not rate-limited by the output of the adsorbent cartridge.

14. A dialysis system, comprising:
an extracorporeal circuit having:
at least a first dialyzer and a second dialyzer, wherein the first dialyzer has fibers with a first pore size, and wherein the second dialyzer is located downstream of a dialysate outlet port of the first dialyzer and has fibers with a second pore size that is smaller than the first pore size;
a first restriction valve located downstream of the dialysate outlet port of the first dialyzer and upstream of the second dialyzer; and
a second restriction valve located downstream of a blood outlet port of the first dialyzer,
wherein the first restriction valve and the second restriction valve are configured to maintain a flow rate of plasma and dialysate from the dialysate outlet port of the first dialyzer below a threshold, wherein the second restriction valve is configured to control a flow rate of blood at the blood outlet port of the first dialyzer to be less than a flow rate of whole blood entering a blood inlet port of the first dialyzer, and wherein restriction action of the second restriction valve is controlled to ensure at least a minimum flow rate of plasma and dialysate is maintained from the dialysate outlet port of the first dialyzer;
a dialysis machine that is fluidly coupled to the first dialyzer and/or the second dialyzer; and
a control unit to control fluid flow rates.

15. The dialysis system according to claim 14, wherein the first dialyzer and the second dialyzer each include a semipermeable membrane, and wherein blood plasma produced by the first dialyzer is directed to an inlet port of the second dialyzer located downstream of the first dialyzer.

16. The dialysis system according to claim 14, further comprising:
a plasma bag, wherein plasma exiting the second dialyzer may enter into the plasma bag for collection.

17. The dialysis system according to claim 14, further comprising:
a recirculation loop that connects the extracorporeal circuit directly after the second dialyzer to the extracorporeal circuit directly before the second dialyzer.

18. The dialysis system according to claim 14, further comprising:
a third dialyzer arranged in parallel with the first dialyzer and/or the second dialyzer.

19. The dialysis system according to claim 14, further comprising:
an adsorbent cartridge disposed downstream of the first dialyzer.

* * * * *